United States Patent
Jensen et al.

(10) Patent No.: US 10,603,296 B1
(45) Date of Patent: Mar. 31, 2020

(54) COMPOSITIONS AND METHODS FOR DIAGNOSIS AND TREATMENT OF NEUROMUSCULAR DISORDERS

(71) Applicants: Eric Dahl Jensen, San Diego, CA (US); Stephanie Venn-Watson, San Diego, CA (US)

(72) Inventors: Eric Dahl Jensen, San Diego, CA (US); Stephanie Venn-Watson, San Diego, CA (US)

(73) Assignee: United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 16/377,993

(22) Filed: Apr. 8, 2019

(51) Int. Cl.
*A61K 31/4164* (2006.01)
*A61K 31/20* (2006.01)
*A61K 31/417* (2006.01)

(52) U.S. Cl.
CPC ............ *A61K 31/20* (2013.01); *A61K 31/417* (2013.01)

(58) Field of Classification Search
CPC ............................. A61K 31/4164; A61K 31/20
USPC .................................................. 514/400, 558
See application file for complete search history.

(56) References Cited

U.S. PATENT DOCUMENTS 5,866,607 A * 2/1999 Harper .................... A61K 31/20 514/558
2018/0318260 A1* 11/2018 Pankow ................ A61K 31/417

OTHER PUBLICATIONS

Zanotti S., et al., Opposing Roles of miR-21 and miR-29 in the Progression of Fibrosis in Duchenne Muscular Dystrophy. Biochim Biophys Acta 1852:1451-1464 (2015).
Eisenberg I, et al. Distinctive Patterns of microRNA Expression in Primary Muscular Disorders. Proc. Natl. Acad. Sci. U. S. A. 104, 17016-17021 (2007).
Perbellini R, et al. Dysregulation and Cellular Mislocalization of Specific miRNAs in Myotonic Dystrophy Type 1. Neuromuscular Disorders. 2011; 21(2):81-88).
Karius T, et al.,MicroRNAs in Cancer Management and Their Modulation by Dietary Agents. Biochem Pharmacol 83:1591-1601 (2012).
Botta-Orlfila T. et al., Identification of Blood Serum micro-RNAs Associated with Idiopathic and LRRK2 Parkinson's Disease. J Neurosci Res 92:1071-1077 (2014).
Di Pietro L. et al, Skeletal Muscle microRNAs as Key Players in the Pathogenesis of Amyotrophic Lateral Sclerosis. Int J Mol Sci 19:1534 (2018).
Ziboh VA et al., Biological Significance of Essential Fatty Acids/ Prostanoids/Lipoxygenase-derived Monohydroxy Fatty Acids in the Skin, Arch Pharm Res 25:747-758 (2002).
Galbiati F et al., Chemical Inhibition of Myristolation of the G-protein Gi1α by 2-hydroxymyristate Does Not Interfere With its Palmitoylation or Membrane Association, Biochem, J. (1996) 313, pp. 717-720 (Printed in Great Britain).
Alexander MS et al., Skeletal Muscle microRNAs: Their Diagnostic and Therapeutic Potential in Human Muscle Diseases. J Neuromusc Dis 2:1-11 (2015).
Deiters, Small Molecule Modifiers of the microRNA and RNA Interference Pathway AAPS J 12:51-60 (2010).

* cited by examiner

*Primary Examiner* — Raymond J Henley, III
(74) *Attorney, Agent, or Firm* — Naval Information Warfare Center, Pacific; Kyle Eppele; Arthur K. Samora

(57) ABSTRACT

Compositions including small molecule biochemicals, and salts and derivatives thereof, and methods for detection, treatment or prophylaxis of neuromuscular disorders are provided, including modulation of microRNA that contribute to neuromuscular disorders, including muscular dystrophies, peripheral motor neuron diseases, motor neuron diseases, neuromuscular junction diseases, myopathies, metabolic diseases of the muscle, amyotrophic lateral sclerosis, multiple sclerosis, Parkinson's disease, motor neuron diseases, Huntington's disease, spinocerebellar ataxia, and spinal muscular atrophy.

9 Claims, 4 Drawing Sheets

COMPOSITIONS AND METHODS FOR DIAGNOSIS AND TREATMENT OF NEUROMUSCULAR DISORDERS

STATEMENT REGARDING FEDERALLY SPONSORED R&D

The United States Government and Epitracker, Inc, have ownership rights in this invention, pursuant to development of a Jointly Made Subject Invention under CRADA Number NCRADA-SSCPACIFIC-17-261.

FIELD OF THE INVENTION

Compositions including small molecule biochemicals, and salts and derivatives thereof, and methods for detection, treatment or prophylaxis of neuromuscular disorders are provided, including modulation of microRNA that contribute to neuromuscular disorders, including muscular dystrophies, peripheral motor neuron diseases, motor neuron diseases, neuromuscular junction diseases, myopathies, metabolic diseases of the muscle, amyotrophic lateral sclerosis, and Parkinson's disease.

BACKGROUND OF THE INVENTION

Neuromuscular disorders are acquired or genetic conditions that affect some part of the neuromuscular system and are typically progressive. Neuromuscular disorders can be categorized as muscular dystrophies, peripheral motor neuron diseases, motor neuron diseases, neuromuscular junction diseases, myopathies, and metabolic diseases of the muscle. Examples of neuromuscular disorders include myotonic dystrophy, amyotrophic lateral sclerosis, and Parkinson's disease. Currently, there are no cures for most neuromuscular disorders. It is generally believed that novel treatments addressing one neuromuscular disorder may also help other neuromuscular disorders.

In general, genetic information from deoxyribonucleic acid (DNA) is transcribed by messenger RNA (mRNA) into proteins. Many neuromuscular diseases, including muscular dystrophies, are caused by genetic mutations that alter mRNA and their resultant proteins that control muscular function. MicroRNA (miRNA) are small, noncoding RNA that can bind to mRNA and post-transcriptionally block DNA- and mRNA-driven activities. As such, miRNA can be targeted to block the effects of genetic mutations, mRNA and resultant proteins that cause neuromuscular diseases. For example, increasing levels of certain miRNAs could be used to downregulate mRNA to treat neuromuscular disorders (see Alexander M S et al., (2015), Skeletal Muscle MicroRNAs: Their Diagnostic and Therapeutic Potential in Human Muscle Diseases, J Neuromusc Dis 2:1-11).

Abnormal levels of specific miRNAs, including lower levels of miR-29c, have been identified as risk factors for and contributors to neuromuscular disorders, such as Duchenne muscular dystrophy, myotonic dystrophy, and nemaline myopathy, Parkinson's disease and rapidly progressive amyotrophic lateral sclerosis. Thus, miR-29c has been proposed as both a blood-based biomarker of and potential therapeutic target for neuromuscular disease.

Notwithstanding the exciting new uses of miRNA, and in particular miR-29c, there have been ongoing barriers related to the delivery of miRNAs to the patient. While direct administration of miRNAs to patients can be challenging due to their inability to cross the gut barrier intact, other small molecules taken orally can influence miRNA activity, enabling the potential for safe and easily administered therapeutics to up- or down-regulate miRNA, which can post-transcriptionally alter gene expression (see Deiters (2010) Small molecule modifiers of the microRNA and RNA interference pathway AAPS J 12:51-60). Please see also Karius et al., MicroRNAs in Cancer Management and Their Modulation by Dietary Agents. Biochem Pharmacol 83:1591-1601 (2012). What is desired is the administration of a small molecule biochemical that can be used to upregulate and raise miR29C in a manner that is therapeutic to a patient suffering from a neuromuscular disease.

SUMMARY OF THE INVENTION

Compositions and methods for the detection, treatment or prophylaxis of neuromuscular disorders are provided. These compositions comprise one or more monohydroxy fatty acids or histidine metabolism intermediates, derivatives of these biochemicals, or salts thereof, which may be administered in combination with other medicaments or as part of various treatment regimens as described herein. The provided compositions are effective for modulating markers of neuromuscular disorders, including raising microRNA-29c. Methods are provided for detecting neuromuscular disorders using blood-based biomarkers and administering the compositions.

Accordingly, in a generally applicable first aspect (i.e., independently combinable with any of the aspects or embodiments identified herein), a pharmaceutical composition is provided comprising: one or more small molecule biochemicals, or pharmaceutically acceptable salts thereof, wherein the one or more small molecule biochemicals are selected from the group consisting of a monohydroxy fatty acid or a histidine metabolism intermediate and a pharmaceutically acceptable carrier.

In an alternative embodiment of the first aspect (i.e., independently combinable with any of the aspects or embodiments identified herein), the one or more small molecules is 2-hydroxymyristate.

In an alternative embodiment of the first aspect (i.e., independently combinable with any of the aspects or embodiments identified herein), the one or more small molecules is N-acetylhistamine.

In an alternative embodiment of the first aspect (i.e., independently combinable with any of the aspects or embodiments identified herein), the composition is in a unit dosage form.

In an alternative embodiment of the first aspect (i.e., independently combinable with any of the aspects or embodiments identified herein), the pharmaceutical composition is configured for administration of from 2.5 mg to 50 mg, per 1 kg of body weight, of the one or more small molecule biochemicals or pharmaceutically acceptable salts thereof to a patient.

In an alternative embodiment of the first aspect (i.e., independently combinable with any of the aspects or embodiments identified herein), the pharmaceutical composition is configured for administration once per day.

In an alternative embodiment of the first aspect (i.e., independently combinable with any of the aspects or embodiments identified herein), the pharmaceutical composition comprises from 0.01 mg to 10000 mg of the one or more small molecule biochemicals or pharmaceutically acceptable salts thereof.

In a generally applicable second aspect (i.e., independently combinable with any of the aspects or embodiments identified herein), use is provided of a pharmaceutical composition of the first aspect or any embodiment thereof, in the manufacture of a medicament for treatment or prophylaxis of neuromuscular disorders, including muscular dystrophies, peripheral motor neuron diseases, motor neuron diseases, neuromuscular junction diseases, myopathies, metabolic diseases of the muscle, Parkinson's disease, and amyotrophic lateral sclerosis.

In an alternative embodiment of the second aspect (i.e., independently combinable with any of the aspects or embodiments identified herein), the use is in the manufacture of a medicament for treatment or prophylaxis of contributors to the presence and severity of neuromuscular disorders, including low miR-29c levels.

In an alternative embodiment of the second aspect (i.e., independently combinable with any of the aspects or embodiments identified herein), the pharmaceutical composition is configured to modulate a marker of neuromuscular disorders or contributors to neuromuscular disorders.

In an alternative embodiment of the second aspect (i.e., independently combinable with any of the aspects or embodiments identified herein), the marker of conditions related to neuromuscular disorders is selected from the group consisting of serum or plasma small molecule metabolite concentration or low serum or plasma miR-29c levels.

In an alternative embodiment of the second aspect (i.e., independently combinable with any of the aspects or embodiments identified herein), the pharmaceutical composition is configured to increase a serum, red blood cell, or tissue concentration of the one or more small molecule biochemicals to between 0.2 μM and 20 μM.

In a generally applicable third aspect (i.e., independently combinable with any of the aspects or embodiments identified herein), a method of treatment or prophylaxis of neuromuscular disorders, including muscular dystrophies, peripheral motor neuron diseases, motor neuron diseases, neuromuscular junction diseases, myopathies, metabolic diseases of the muscle, Parkinson's disease, and amyotrophic lateral sclerosis, and other related conditions, comprising: administering to a patient in need thereof, an effective amount of monohydroxy fatty acids or histadine metabolism intermediates, or pharmaceutically acceptable salts thereof, wherein the one or more small molecule biochemicals are selected from monohydroxy fatty acids or histadine metabolism intermediates.

In an alternative embodiment of the third aspect (i.e., independently combinable with any of the aspects or embodiments identified herein), the one or more small molecule biochemicals or pharmaceutically acceptable salts thereof is provided as a pharmaceutical composition in a unit dosage form comprising the one or more monohydroxy fatty acids or histadine metabolism intermediates or pharmaceutically acceptable salts thereof and a pharmaceutically acceptable carrier.

In an alternative embodiment of the third aspect (i.e., independently combinable with any of the aspects or embodiments identified herein), the unit dosage form comprises from 0.01 mg to 10000 mg of the one or more monohydroxy fatty acids or histadine metabolism intermediates or pharmaceutically acceptable salts thereof.

In an alternative embodiment of the third aspect (i.e., independently combinable with any of the aspects or embodiments identified herein), the one or more monohydroxy fatty acids or histadine metabolism intermediates described herein.

In an alternative embodiment of the third aspect (i.e., independently combinable with any of the aspects or embodiments identified herein), the pharmaceutical composition comprises a plurality of different monohydroxy fatty acids or histadine metabolism intermediates described herein.

In an alternative embodiment of the third aspect (i.e., independently combinable with any of the aspects or embodiments identified herein), from 2.5 mg to 50 mg of the one or more monohydroxy fatty acids or histadine metabolism intermediates or pharmaceutically acceptable salts thereof is administered to the patient, per 1 kg of body weight, per day.

In an alternative embodiment of the third aspect (i.e., independently combinable with any of the aspects or embodiments identified herein), the one or more monohydroxy fatty acids or histadine metabolism intermediates or pharmaceutically acceptable salts thereof is administered to the patient once per day.

In an alternative embodiment of the third aspect (i.e., independently combinable with any of the aspects or embodiments identified herein), a serum, tissue, or a red blood cell membrane concentration of the one or more small molecule biochemicals is increased 1.25 to 6 times above the patient's baseline levels to achieve concentrations between 0.5 μM and 20 μM.

In a generally applicable fourth aspect (i.e., independently combinable with any of the aspects or embodiments identified herein), a composition substantially as described herein is provided.

In a generally applicable fifth aspect (i.e., independently combinable with any of the aspects or embodiments identified herein), a use substantially as described herein is provided.

DESCRIPTION OF THE DRAWINGS

The novel features of the present invention will be best understood from the accompanying drawings, taken in conjunction with the accompanying description, in which similarly-referenced characters can refer to similarly-referenced parts, and in which.

DETAILED DESCRIPTION OF THE EMBODIMENTS

Figure 1A:
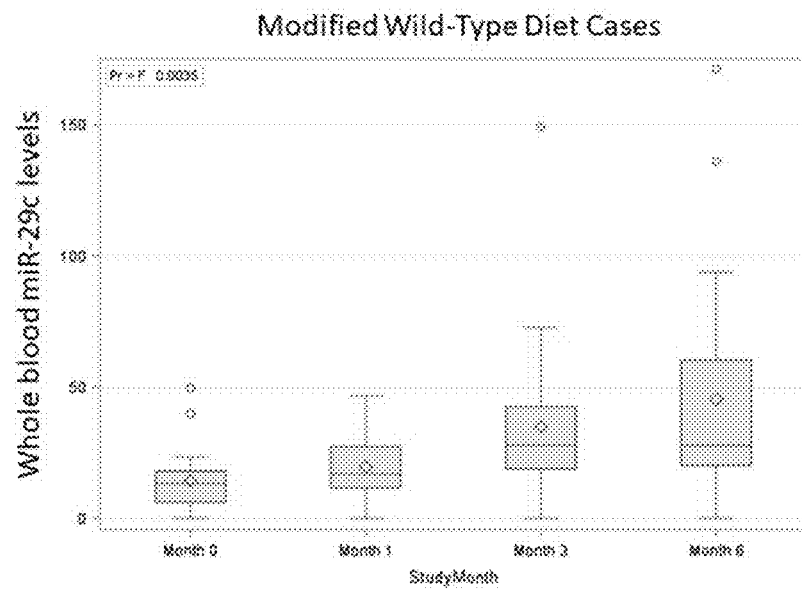
FIG. 1A can provide data on increasing blood microRNA-29c levels in dolphins on a modified fish diet.

Small molecule biochemicals can regulate microRNA (miRNA), and miRNA can regulate messenger RNA's (mRNA) translation of proteins associated with diseases, including neuromuscular disorders. Thus, mRNA-driven diseases may be treated by administering small molecule biochemicals that upregulate specific miRNA. Compositions are provided, including one or more monohydroxy fatty acids or histadine metabolism intermediates (i.e. small molecule biochemicals), that may be administered to raise miR-29c blood levels to prevent or treat neuromuscular disorders and contributors to neuromuscular disorders. Methods are also provided to detect the risk of neuromuscular disorders and other related conditions.

MiR-29c is a microRNA that provides multiple benefits, including as an antifibrotic (Zanotti S., et al., Opposing Roles of miR-21 and miR-29 in the Progression of Fibrosis in Duchenne Muscular Dystrophy), and lower miR-29c has been associated with Duchenne muscular dystrophy and nemaline myopathy (Eisenberg I. et al., Distinctive Patterns of microRNA Expression in Primary Muscular Disorders. Proc. Natl. Acad. Sci. U.S.A. 104, 17016-17021). Lowered miR-29c has been detected in muscle biopsies of myotonic dystrophy type 1 patients (Perbellini R, et al. Dysregulation and Cellular Mislocalization of Specific MiRNAs in Myotonic Dystrophy Type 1. Neuromuscular Disorders. 2011; 21(2):81-88). Lower miR-29c has also been reported in Parkinson's disease and rapidly progressing amyotrophic lateral sclerosis (Botta-Orlfila T et al., Identification of blood serum micro-RNAs associated with idiopathic and LRRK2 Parkinson's Disease, J Neurosci Res 92:1071-1077 (2014); Di Pietro L et al., Skeletal Muscle microRNAs as Key Players in the Pathogenesis of Amyotrophic Lateral Sclerosis. Int J Mol Sci 19:1534 (2018). As known in the prior art, miR-29c can target proenkephalin, alpha2, and trophinin genes and can be downregulated during physical inactivity and muscle atrophy. As such, interventions to upregulate miR-29c have been proposed in the prior art to treat neuromuscular diseases, including components of muscle-specific fibrosis.

Monohydroxy fatty acids are fatty acids having a hydroxy substituent. As an example, a 2-hydroxy fatty acid has the hydroxy substituent at C-2, and a 3-hydroxy fatty acid has the hydroxy substituent at C-3. Long chain monohydroxy fatty acids refers without limitation to a fatty acid with 13-22 carbon atoms. As an example, 2-hydroxymyristate is a long chain 2-hydroxy fatty acid that is assumed to be present in humans but has not been measured. Monohydroxy fatty acids derivatives of polyunsaturated fatty acids, such as 15S-HETrE, have been identified as metabolites in the skin which can be incorporated into the cell membrane and may exert anti-inflammatory or antiproliferative effects by modulating protein kinase C and nuclear MAP-kinase/AP-1/apoptotic signaling events (See Ziboh et al., Biological Significance of Essential Fatty Acids/Prostanoids/Lipoxygenase-Derived Monohydroxy Fatty Acids in The Skin. Arch Pharm Res 25:747-758). 2-hydroxymyristate inhibits myristoylation of the G-protein $G_{i1\alpha}$, but its therapeutic value has not been well explored (See Galbiati F et al., Chemical Inhibition of Myristolation of the G-protein $G_{i1\alpha}$ by 2-hydroxymyristate Does Not Interfere with its Palmitoylation or Membrane Association Biochem J 313:717-720). Per Galbiati et al., there can be indications that palmitoylation, but not myristoylation, regulates membrane attachment.

The histadine metabolism pathway can involve the metabolism of histadine, an essential amino acid involved in protein biosynthesis, to histamine. Histadine metabolism intermediates include hydantoin-5-proprionic acid, trans-urocanate, imidazole propionate, formiminoglutamate, imidazole lactate, N-acetylcarnosine, anserine, 1-methyl-4-imidazoleacetate, 1-ribosyl-imidazoleacetate, 4-imidazoleacetate and N-acetylhistamine. N-acetylhistamine has been detected but not quantified in humans, and its therapeutic value has not been well explored.

It can be an object of certain of the embodiments to provide a method for detecting protective factors for and risk factors against neuromuscular disorders provided herein, including but not limited to muscular dystrophies, peripheral motor neuron diseases, motor neuron diseases, neuromuscular junction diseases, myopathies, metabolic diseases of the muscle, amyotrophic lateral sclerosis, Parkinson's disease, and spinal muscular atrophy, and conditions that cause and exacerbate neuromuscular disorders, including but not limited to elevated or low microRNA-29c, and other related conditions in mammal subjects, such as companion animals and humans.

An object of certain of the embodiments can be to provide a method for detecting neuromuscular disorders and associated conditions in mammal subjects, such as companion animals and humans. It is an object of certain of the embodiments to provide a method for increasing the serum, plasma, or erythrocyte membrane level of one or more small molecule biochemicals or small molecule metabolite derivatives, including but not limited to a histadine metabolism intermediate, for example, an amino acid, such as N-acetylhistamine, and/or certain monohydroxy fatty acids, such as 2-hydroxymyristate, in mammal subjects, such as companion animals and humans. An object of certain of the embodiments can further be to provide a small molecule metabolite supplement or prescription therapeutic for treating or preventing neuromuscular disorders and associated conditions. An object of certain of the embodiments can be to provide a method for detecting and/or treating neuromuscular disorders and associated conditions in mammal subjects, such as companion animals and humans, that is easy to accomplish in a cost-effective manner.

An object of certain of the embodiments can be to provide a method for modulating markers of neuromuscular disorders and associated conditions in mammal subjects, such as companion animals and humans. An object of certain of the embodiments can be to provide a method for detecting neuromuscular disorders and associated conditions in mammal subjects, such as companion animals and humans. An object of certain of the embodiments can be to provide a method for treatment of neuromuscular disorders and associated conditions in mammal subjects, such as companion animals and humans. An object of certain of the embodiments can be to provide a method for prophylaxis of neuromuscular disorders and associated conditions in mammal subjects, such as companion animals and humans. An object of certain of the embodiments can be to provide a method for prophylaxis of neuromuscular disorders and associated conditions, including low miR-29c, and other related conditions, in mammal subjects, such as companion animals and humans.

An object of certain of the embodiments can be to provide a method for increasing a monohydroxy fatty acid or a histadine metabolism intermediate, in the sera, plasma, or erythrocyte membranes of mammal subjects, such as companion animals and humans. An object of certain of the embodiments can be to provide a method for detecting or treating neuromuscular disorders and associated conditions in mammal subjects, such as companion animals and humans. An object of certain of the embodiments can be to provide a monohydroxy fatty acid or a histadine metabolism intermediate, substantially free from other small molecule biochemicals in mammal subjects, such as companion animals and humans.

It can be an object of certain of the embodiments can be to provide a method for detecting and treating neuromuscular disorders and associated conditions in mammal subjects, such as companion animals and humans. An object of certain of the embodiments can be to provide a monohydroxy fatty acid, such as 2-hydroxymyristate, or a histadine metabolism intermediate, such as N-acetylhistamine, for treating neuromuscular disorders and associated conditions in mammal subjects, such as companion animals and humans. An object of certain of the embodiments can be to provide a method for prophylaxis of neuromuscular disorders and associated conditions in mammal subjects, such as companion animals and humans. An object of certain of the embodiments can be to provide a method for detecting neuromuscular disorders and associated conditions in mammal subjects, such as companion animals and humans. An object of certain of the embodiments can be to provide a monohydroxy fatty acid or a histadine metabolism intermediate as described herein to supplement for managing neuromuscular disorders and associated conditions, such as for companion animals and humans.

An object of certain of the embodiments can be to provide a bioavailable form of monohydroxy fatty acids or histadine metabolism intermediates to mammal subjects, such as companion animals and humans. An object of certain of the embodiments can be to provide one or more monohydroxy fatty acids or histadine metabolism intermediates described herein with one or more other monohydroxy fatty acids or histadine metabolism intermediates described herein to mammal subjects, such as companion animals and humans. An object of certain embodiments can be to provide a method for increasing monohydroxy fatty acids or histadine metabolism intermediates described herein in the sera of mammal subjects, such as companion animals and humans. An object of certain of the embodiments can be to provide a method for altering concentrations of a variety of monohydroxy fatty acids or histadine metabolism intermediates as described herein in the sera, plasma, or erythrocyte membranes of mammal subjects, such as companion animals and humans.

Compositions including one or more monohydroxy fatty acids or histadine metabolism intermediates, and associated methods for treatment of neuromuscular disorders are provided. Compositions including one or more bioavailable monohydroxy fatty acids or histadine metabolism intermediates are provided.

Compositions including one or more monohydroxy fatty acids, such as 2-hydroxymyristate, or histadine metabolism intermediates, such as N-acetylhistamine, and associated methods for treatment of diseases driven by low miR-146a are provided. Compositions including one or more bioavailable biochemicals contained herein are provided.

Compositions including one or more monohydroxy fatty acids, such as 2-hydroxymyristate, or histadine metabolism intermediates, such as N-acetylhistamine, and associated methods for treatment of fibrotic diseases, including fibrosis with Duchenne muscular dystrophy, are provided. Compositions including one or more bioavailable monohydroxy fatty acids or histadine metabolism intermediates are provided.

One or more than one of the aforementioned objects is provided by or achieved by the various compositions, methods, and uses as described herein.

Definitions

The term "alcohol" as used herein is a broad term, and is to be given its ordinary and customary meaning to a person of ordinary skill in the art (and is not to be limited to a special or customized meaning), and refers without limitation to any compound as described herein incorporating one or more hydroxy groups, or being substituted by or functionalized to include one or more hydroxy groups.

The term "long-chain fatty acid" as used herein is a broad term, and is to be given its ordinary and customary meaning to a person of ordinary skill in the art (and is not to be limited to a special or customized meaning), and refers without limitation to a fatty acid with 13-22 carbon atoms.

The term "derivative" as used herein is a broad term, and is to be given its ordinary and customary meaning to a person of ordinary skill in the art (and is not to be limited to a special or customized meaning), and refers without limitation to any compound as described herein incorporating one or more derivative groups, or being substituted by or functionalized to include one or more derivative groups. Derivatives include but are not limited to esters, amides, anhydrides, acid halides, thioesters, phosphates, triphosphates, and β-sulfenyl derivatives.

The term "hydrocarbon" as used herein is a broad term, and is to be given its ordinary and customary meaning to a person of ordinary skill in the art (and is not to be limited to a special or customized meaning), and refers without limitation to any moiety comprising only carbon and hydrogen atoms. A functionalized or substituted hydrocarbon moiety has one or more substituents as described elsewhere herein.

The term "lipid" as used herein is a broad term, and is to be given its ordinary and customary meaning to a person of ordinary skill in the art (and is not to be limited to a special or customized meaning), and refers without limitation to saturated and unsaturated oils and waxes, derivatives, amides, glycerides, small molecule biochemicals, fatty alcohols, sterol and sterol derivatives, phospholipids, ceramides, sphingolipids, tocopherols, and carotenoids, among others.

The terms "pharmaceutically acceptable" as used herein is a broad term, and is to be given its ordinary and customary meaning to a person of ordinary skill in the art (and is not to be limited to a special or customized meaning), and refers without limitation to those compounds, materials, compositions, and/or dosage forms which are, within the scope of sound medical judgment, suitable for contact with the tissues of and/or for consumption by human beings and animals without excessive toxicity, irritation, allergic response, or other problem complications commensurate with a reasonable risk/benefit ratio.

The terms "pharmaceutically acceptable salts" and "a pharmaceutically acceptable salt thereof" as used herein are broad terms, and are to be given their ordinary and customary meaning to a person of ordinary skill in the art (and is not to be limited to a special or customized meaning), and refer without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity. In addition to salts, pharmaceutically acceptable precursors and derivatives of the compounds can be employed. Pharmaceutically acceptable amides, lower alkyl derivatives, and protected derivatives can also be suitable for use in compositions and methods of preferred embodiments. While it may be possible to administer the compounds of the preferred embodiments in the form of pharmaceutically acceptable salts, it is generally preferred to administer the compounds in neutral form.

The term "pharmaceutical composition" as used herein is a broad term, and is to be given its ordinary and customary meaning to a person of ordinary skill in the art (and is not to be limited to a special or customized meaning), and refers without limitation to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids or bases. Pharmaceutical compositions will generally be tailored to the specific intended route of administration.

The term "carrier" as used herein is a broad term, and is to be given its ordinary and customary meaning to a person of ordinary skill in the art (and is not to be limited to a special or customized meaning), and refers without limitation to a compound that facilitates the incorporation of a compound into cells or tissues. For example, without limitation, dimethyl sulfoxide (DMSO) is a commonly utilized carrier that facilitates the uptake of many organic compounds into cells or tissues of a subject. Water, saline solution, ethanol, and mineral oil are also carriers employed in certain pharmaceutical compositions.

The term "diluent" as used herein is a broad term, and is to be given its ordinary and customary meaning to a person of ordinary skill in the art (and is not to be limited to a special or customized meaning), and refers without limitation to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

The term "excipient" as used herein is a broad term, and is to be given its ordinary and customary meaning to a person of ordinary skill in the art (and is not to be limited to a special or customized meaning), and refers without limitation to a substance that is added to a pharmaceutical composition to provide, without limitation, bulk, consistency, stability, binding ability, lubrication, disintegrating ability etc., to the composition. A "diluent" is a type of excipient.

The term "subject" as used herein is a broad term, and is to be given its ordinary and customary meaning to a person of ordinary skill in the art (and is not to be limited to a special or customized meaning), and refers without limitation to an animal that is the object of treatment, observation or experiment. "Animal" includes cold- and warm-blooded vertebrates and invertebrates such as fish, shellfish, reptiles and, in particular, mammals. "Mammal" includes, without limitation, dolphins, mice, rats, rabbits, guinea pigs, dogs, cats, sheep, goats, cows, horses, primates, such as monkeys, chimpanzees, and apes, and, in particular, humans. In some embodiments, the subject is human.

The terms "treating," "treatment," "therapeutic," or "therapy" as used herein are broad terms, and are to be given their ordinary and customary meaning (and are not to be limited to a special or customized meaning) and, without limitation, do not necessarily mean total cure or abolition of the disease or condition. Any alleviation of any undesired markers, signs or symptoms of a disease or condition, to any extent, can be considered treatment and/or therapy. Furthermore, treatment may include acts that may worsen the patient's overall feeling of well-being or appearance.

The terms "therapeutically effective amount" and "effective amount" as used herein are broad terms, and are to be given its ordinary and customary meaning to a person of ordinary skill in the art (and are not to be limited to a special or customized meaning), and are used without limitation to indicate an amount of an active compound, or pharmaceutical agent, that elicits the biological or medicinal response indicated. For example, a therapeutically effective amount of compound can be the amount needed to prevent, alleviate or ameliorate markers or symptoms of a condition or prolong the survival of the subject being treated. This response may occur in a tissue, system, animal or human and includes alleviation of the signs or symptoms of the disease being treated. Determination of a therapeutically effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

The term "solvents" as used herein is a broad term, and is to be given its ordinary and customary meaning to a person of ordinary skill in the art (and is not to be limited to a special or customized meaning), and refers without limitation to compounds with some characteristics of solvency for other compounds or means, that can be polar or nonpolar, linear or branched, cyclic or aliphatic, aromatic, naphthenic and that includes but is not limited to: alcohols, derivatives, diesters, ketones, acetates, terpenes, sulfoxides, glycols, paraffins, hydrocarbons, anhydrides, heterocyclics, among others.

Any percentages, ratios or other quantities referred to herein are on a weight basis, unless otherwise indicated.

Small Molecule Biochemicals

Small molecule biochemicals can be defined as low molecular weight (typically less than 900 Daltons, but sometimes higher) and can include, but not limited to, amino acids (including but not limited to N-acetylhistamine), lipids (including but not limited to monohydroxy fatty acids, such as 2-hydroxymyristate), nucleotides, peptides, carbohydrates or xenobiotics that can be identified and measured in the body and as provided herein. Small molecule biochemicals can originate from ingestion of food or other oral products or produced endogenously. Small molecule biochemicals are referred to and described using conventional nomenclature as is employed by one of skill in the art.

A small molecule metabolite may be referred to by various names, for example, N-acetylhistamine may be referred to as 4-(2-Acetamidoethyl)imidazole.

In some embodiments, the small molecule metabolite can be an amino acid or lipid as provided herein. In further embodiments, one or more small molecule biochemicals can include at least one amino acid or lipid as provided herein.

Small molecule biochemicals that are ideal candidates as both biomarkers and therapeutics are biochemicals that are successfully detected in serum at high nanomolar or micromolar levels that have a low molecular weight (<900 Daltons) and meet Lipinski's rule of five. All biochemicals provided herein meet these criteria.

In some embodiments, a small molecule metabolite can be histadine metabolism intermediates and amino acids, including but not limited to hydantoin-5-proprionic acid, trans-urocanate, imidazole propionate, formiminoglutamate, imidazole lactate, N-acetylcarnosine, anserine, 1-methyl-4-imidazoleacetate, 1-ribosyl-imidazoleacetate, 4-imidazoleacetate and N-acetylhistamine. Derivatives can be synthesized by published methods.

In some embodiments, a small molecule metabolite can be lipid, including but not limited to monohydroxy fatty acids, including but not limited to 2-hydroxyoctanoate, 2-hydroxymyristate, 5-hydroxyhexanoate, 5-hydroxydecanoate, 8-hydroxyoctanoate and 16-hydroxypalmitate, Derivatives can be synthesized by published methods.

In some embodiments, a monohydroxy fatty acid or histadine metabolism intermediate is provided in a bioavailable form. The term "bioavailability" refers to the fraction of an administered dose of unchanged drug that reaches the systemic circulation, one of the principal pharmacokinetic properties of drugs. By definition, when a medication is administered intravenously, its bioavailability is 100%. As employed herein, the term "bioavailable" refers to a form of the small molecule metabolite that is successfully absorbed by the body when using methods of administration other than intravenous, for example, an oral therapeutic). In some embodiments, a monohydroxy fatty acid or histadine metabolism intermediate-based compositions may include adaptions that optimize absorption.

A pure or purified monohydroxy fatty acid or histadine metabolism intermediate may exist in various physical states. For example, N-acetylhistamine exists as a powder that is stable at room temperature; this compound can be purchased in forms suitable for research purposes in small amounts from some commercial suppliers (for example, from Sigma-Aldrich Corp., of St. Louis, Mo.). Other small molecule biochemicals, or stereoisomers, or solvates, or esters, or salts or other derivatives thereof, may exist as oils, solids, crystalline solids, or gases.

A monohydroxy fatty acid or histadine metabolism intermediate or the pharmaceutically acceptable salts or derivatives thereof, may be provided in a purity (e.g., a percentage of the small molecule metabolite, or its pharmaceutically acceptable salts or derivatives, in a bulk form) of at least about 10%, at least about 20%, at least about 30%, at least about 40%, at least about 50%, at least about 60%, at least about 70%, at least about 80%, at least about 90%, at least about 95%, at least about 98%, at least about 99%, at least about 99.9%, at least about 99.99%, or substantially pure, wherein substantially pure may include, but not be limited to, a product with impurities at a level such that no physiological effect from the presence of the impurities is detectable. A mixture of a monohydroxy fatty acid or histadine metabolism intermediate, such as, for example, an amino acid and/or lipid, or pharmaceutically acceptable salts or derivatives thereof, may be present in a purity of at least about 10%, at least about 20%, at least about 30%, at least about 40%, at least about 50%, at least about 60%, at least about 70%, at least about 80%, at least about 90%, at least about 95%, at least about 98%, at least about 99%, at least about 99.9%, at least about 99.99%, or substantially pure. The small molecule metabolite, or a mixture thereof, or a pharmaceutically acceptable salt or derivative thereof, may be free from other small molecule biochemicals. Without limitation, a monohydroxy fatty acid or histidine metabolism intermediate as provided herein may be substantially free from other small molecule biochemicals, singly or taken as a group; small molecule biochemicals to exclude, for example, can include monohydroxy fatty acids containing polyunsaturated fatty acids. In some embodiments, a monohydroxy fatty acid or histidine metabolism intermediate as provided herein may be substantially free from other species of amino acids or lipids not included herein.

A monohydroxy fatty acid, such as 2-hydroxymyristate, or a histidine metabolism intermediate, such as N-acetylhistamine, or a pharmaceutically acceptable salt or derivative thereof, may be from any source. In some embodiments, a monohydroxy fatty acid or a histidine metabolism intermediate, or its pharmaceutically acceptable salts or derivatives, may be present in natural sources, may be isolated from natural sources, may be semi-synthetic, may be synthetic, or may be a mixture of one or more of these. The monohydroxy fatty acid or histidine metabolism intermediate, or its pharmaceutically acceptable salts or derivatives, may be produced in a laboratory, may be produced in nature, may be produced by enzymatic processes, may be produced by wild microbes, may be produced by genetically modified microbes, may be isolated from animal tissues, may be produced by chemical synthesis, or may be produced by a plurality of these processes.

The monohydroxy fatty acid or histidine metabolism intermediate may be derived from natural sources, e.g., fish oils, or can be synthesized by methods as are known in the art. In some embodiments, the monohydroxy fatty acid or histidine metabolism intermediate may be contaminated with undesired components present in unrefined or unpurified natural products. In such situations, it can be desirable to remove undesired components, or to increase the concentration of desired components using known separation or purification techniques.

In any compound described herein, all tautomeric forms are also intended to be included. Without limitation, all tautomers of carboxylic groups are intended to be included.

In any compound described herein having one or more double bond(s) generating geometrical isomers that can be defined as E or Z, each double bond may independently be E or Z, or a mixture thereof.

Where compounds disclosed herein have unfilled valencies, then the valencies are to be filled with hydrogens or isotopes thereof, e.g., hydrogen-1 (protium) and hydrogen-2 (deuterium).

The monohydroxy fatty acid, such as 2-hydroxymyristate, or the histidine metabolism intermediate, such as N-acetylhistamine, as described herein, includes crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like.

Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

The compounds described herein can be labeled isotopically. In some circumstances, substitution with isotopes such as deuterium may afford certain therapeutic advantages resulting from greater metabolic stability, such as, for example, increased in vivo half-life or reduced dosage requirements. Isotopic substitution may be beneficial in monitoring subject response to administration of a compound, for example, by providing opportunity for monitoring of the fate of an atom in a compound. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Pharmaceutical Compositions Including One or More Small Molecule Biochemicals

Formulations including a monohydroxy fatty acid, such as 2-hydroxymyristate, or a histadine metabolism intermediate, such as N-acetylhistamine or a salt or derivative thereof, and at least one excipient is provided. It is generally preferred to administer the compounds of the embodiments in oral formulations; however, other routes of administration are also contemplated.

The pharmaceutical compositions described herein can be administered by themselves to a subject, or in compositions where they are mixed with other active agents, as in combination therapy, or with carriers, diluents, excipients or combinations thereof. Formulation is dependent upon the route of administration chosen. Techniques for formulation and administration of the compounds described herein are known to those skilled in the art (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

The pharmaceutical compositions disclosed herein may be manufactured by a process that is itself known, e.g., by means of conventional mixing, dissolving, granulating, dragee-making, levigating, emulsifying, encapsulating, entrapping, tableting, or extracting processes. Many of the compounds used in the pharmaceutical combinations disclosed herein may be provided as salts with pharmaceutically acceptable counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Contemplated herein is any combination of the forgoing, or other methods as would be known to one of ordinary skill in the art (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

In practice, a monohydroxy fatty acid, such as 2-hydroxymyristate, or a histadine metabolism intermediate, such as N-acetylhistamine or a salt or derivative thereof, may be combined as the active ingredient in intimate admixture with a pharmaceutical carrier according to conventional pharmaceutical compounding techniques. The carrier can take a wide variety of forms depending on the form of preparation desired for administration. Thus, the pharmaceutical compositions provided herein can be presented as discrete units suitable for oral administration such as capsules, cachets or tablets each containing a predetermined amount of the active ingredient. Further, the compositions can be presented as an oil, a powder, as granules, as a solution, as a suspension in an aqueous liquid, as a non-aqueous liquid, as an oil-in-water emulsion, or as a water-in-oil liquid emulsion. In addition to the common dosage forms set out above, the compounds provided herein, or pharmaceutically acceptable salts or derivatives thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

A formulation may also be administered in a local rather than systemic manner, for example, via injection of the compound directly into the infected area, often in a depot or sustained release formulation. Furthermore, a targeted drug delivery system might be used, for example, in a liposome coated with a tissue specific antibody.

The pharmaceutical compositions may contain a monohydroxy fatty acid, such as 2-hydroxymyristate, or a histadine metabolism intermediate, such as N-acetylhistamine or a salt or derivative thereof, in an amount effective for the desired therapeutic effect. In some embodiments, the pharmaceutical compositions are in a unit dosage form and comprise from about 0.1 mg or less to about 5000 mg or more per unit dosage form. In further embodiments, the pharmaceutical compositions comprise from about 1 to about 500 mg per unit dosage form or from about 500 to 5000 mg per unit dosage form. Such dosage forms may be solid, semisolid, liquid, an emulsion, or adapted for delivery via aerosol or the like for inhalation administration.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, lower alcohols, and water. Examples of gaseous carriers include carbon dioxide and nitrogen.

Pharmaceutical compositions provided herein can be prepared as solutions or suspensions of the active compound(s) in water. A suitable surfactant can be included such as, for example, hydroxypropylcellulose. Dispersions can also be prepared in glycerol, liquid polyethylene glycols, and mixtures thereof in oils. Further, a preservative can be included to, for example, prevent the detrimental growth of microorganisms.

Pharmaceutical compositions provided herein suitable for injectable use include sterile aqueous solutions or dispersions. Furthermore, the compositions can be in the form of sterile powders for the extemporaneous preparation of such sterile injectable solutions or dispersions. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound provided herein, or pharmaceutically acceptable salt or derivative thereof, can also be prepared in powder or liquid concentrate form for dilution.

The monohydroxy fatty acid, such as 2-hydroxymyristate, or the histadine metabolism intermediate, such as N-acetylhistamine contained herein, or a salt or derivative thereof, can be formulated as a liposome. The small molecule metabolite can be a component of the lipid portion of the liposome or can be encapsulated in the aqueous portion of the liposome. The monohydroxy fatty acid, such as 2-hydroxymyristate, or the histadine metabolism intermediate, such as N-acetylhistamine contained herein, or a salt or derivative thereof, can also be coformulated with a cyclodextrin. The cyclodextrin can be, for example, hydroxypropyl-β-cyclodextrin or a sulfobutylether cyclodextrin.

Contemplated herein are compositions including a monohydroxy fatty acid, such as 2-hydroxymyristate, or a histadine metabolism intermediate, such as N-acetylhistamine contained herein, or a salt or derivative thereof in combination with at least one additional active agent. A monohydroxy fatty acid, such as 2-hydroxymyristate, or a histadine metabolism intermediate, such as N-acetylhistamine, or a salt or derivative thereof, and the at least one additional active agent(s) may be present in a single formulation or in multiple formulations provided together, or may be unformulated (for example, free of excipients and carriers). In some embodiments, a monohydroxy fatty acid, such as 2-hydroxymyristate, or a histadine metabolism intermediate, such as N-acetylhistamine, or a salt or derivative thereof, can be administered with one or more additional agents together in a single composition. For example, a compound of a monohydroxy fatty acid, such as 2-hydroxymyristate, or a histadine metabolism intermediate, such as N-acetylhistamine, or a salt or derivative thereof, can be administered in one composition, and at least one of the additional agents can be administered in a second composition. In a further embodiment, a monohydroxy fatty acid, such as 2-hydroxymyristate, or a histadine metabolism intermediate, such as N-acetylhistamine, or a salt or derivative thereof and the at least one additional active agent(s) are co-packaged in a kit. For example, a drug manufacturer, a drug reseller, a physician, a compounding shop, or a pharmacist can provide a kit comprising a disclosed compound or product and another component for delivery to a patient.

Some embodiments described herein relate to a pharmaceutical composition, which can include a therapeutically effective amount of one or more compounds described herein (e.g. a monohydroxy fatty acid, such as 2-hydroxymyristate, or a histadine metabolism intermediate, such as N-acetylhistamine or a pharmaceutically acceptable salt or derivative thereof) and a pharmaceutically acceptable carrier, diluent, excipient or combination thereof. The pharmaceutical composition can include a monohydroxy fatty acid, such as 2-hydroxymyristate, or a histadine metabolism intermediate, such as N-acetylhistamine, or a salt or derivative thereof in, for example, >1%, ≥2%, ≥3%, ≥4%, ≥5%, ≥6%, ≥7%, ≥8%, ≥9%, ≥10%, ≥20%, ≥30%, ≥40%, ≥50%, ≥60%, ≥70%, ≥80%, ≥90%, ≥95%, or ≥98% of the composition. In some embodiments, the pharmaceutical composition can include a plurality of a monohydroxy fatty acid, such as 2-hydroxymyristate, and/or a histadine metabolism intermediate, such as N-acetylhistamine described herein, or salts or derivatives thereof in, for example, >1%, ≥2%, ≥3%, ≥4%, ≥5%, ≥6%, ≥7%, ≥8%, ≥9%, ≥10%, ≥20%, ≥30%, ≥40%, ≥50%, ≥60%, ≥70%, ≥80%, ≥90%, ≥95%, or ≥98% of the composition.

Other Dosage Forms

The compositions for topical administration comprise a molecule of one or more of the embodiments and a dermatologically acceptable vehicle. The vehicle may be aqueous or nonaqueous. The dermatologically acceptable vehicle used in the topical composition may be in the form of a lotion, a gel, an ointment, a liquid, a cream, or an emulsion. If the vehicle is an emulsion, the emulsion may have a continuous aqueous phase and a discontinuous nonaqueous or oil phase (oil-in-water emulsion), or a continuous nonaqueous or oil phase and a discontinuous aqueous phase (water-in-oil emulsion). When administered topically in liquid or gel form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain coloring and scenting agents.

In certain embodiments, a silicone elastomer (e.g., dimethicone cross polymer) is employed to increase delivery and penetration of the molecule into the skin. The pharmaceutical excipients used in the topical preparations of the compositions may be selected from the group consisting of solvents, emollients and/or emulsifiers, oil bases, preservatives, antioxidants, tonicity adjusters, penetration enhancers and solubilizers, chelating agents, buffering agents, surfactants, one or more polymers, and combinations thereof.

Suitable solvents for an aqueous or hydrophilic topical formulation include water; ethyl alcohol; isopropyl alcohol; mixtures of water and ethyl and/or isopropyl alcohols; glycerin; ethylene, propylene or butylene glycols; DMSO; and mixtures thereof. Suitable solvents for hydrophobic topical formulations include mineral oils, vegetable oils, and silicone oils. If desired, the compositions as described herein may be dissolved or dispersed in a hydrophobic oil phase, and the oil phase may then be emulsified in an aqueous phase comprising water, alone or in combination with lower alcohols, glycerin, and/or glycols. Anhydrous formulations may also be employed; however, in certain embodiments it may be acceptable to provide water based compositions, or to permit a limited amount of water to be present.

Viscosity of the compositions can be maintained at the selected level using a pharmaceutically acceptable thickening agent. Suitable viscosity enhancers or thickeners which may be used to prepare a viscous gel or cream with an aqueous base include sodium polyacrylate, xanthan gum, polyvinyl pyrrolidone, acrylic acid polymer, carragenans, hydroxyethyl cellulose, hydroxypropyl cellulose, methyl cellulose, ethyl cellulose, propyl cellulose, hydroxypropyl methyl cellulose, polyethoxylated polyacrylamides, polyethoxylated acrylates, and polyethoxylated alkane thiols. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the thickening agent selected. An amount is preferably used that will achieve the selected viscosity. Viscous compositions are normally prepared from solutions by the addition of such thickening agents, or by employing a base that has an acceptable level of viscosity.

Suitable emollients include hydrocarbon oils and waxes such as mineral oil, petrolatum, paraffin, ceresin, ozokerite, microcrystalline wax, polyethylene, squalene, perhydrosqualene, silicone oils, triglyceride esters, acetoglyceride esters, such as acetylated monoglycerides; ethoxylated glycerides, such as ethoxylated glyceryl monostearate; alkyl esters of fatty acids or dicarboxylic acids.

Suitable silicone oils for use as emollients include dimethyl polysiloxanes, methyl(phenyl) polysiloxanes, and water-soluble and alcohol-soluble silicone glycol copolymers. Suitable triglyceride esters for use as emollients include vegetable and animal fats and oils including castor oil, safflower oil, cotton seed oil, corn oil, olive oil, cod liver oil, almond oil, avocado oil, palm oil, sesame oil, and soybean oil.

Suitable esters of carboxylic acids or diacids for use as emollients include methyl, isopropyl, and butyl esters of fatty acids. Specific examples of alkyl esters including hexyl laurate, isohexyl laurate, iso-hexyl palmitate, isopropyl palmitate, decyl oleate, isodecyl oleate, hexadecyl stearate, decyl stearate, isopropyl isostearate, dilauryl lactate, myristyl lactate, and cetyl lactate; and alkenyl esters of fatty acids such as oleyl myristate, oleyl stearate, and oleyl oleate. Specific examples of alkyl esters of diacids include diisopropyl adipate, diisohexyl adipate, bis(hexyldecyl) adipate, and diisopropyl sebacate.

Other suitable classes of emollients or emulsifiers which may be used in the topical formulations include fatty acids, fatty alcohols, fatty alcohol ethers, ethoxylated fatty alcohols, fatty acid esters of ethoxylated fatty alcohols, and waxes.

Specific examples of fatty acids for use as emollients include pelargonic, lauric, myristic, palmitic, stearic, isostearic, hydroxystearic, oleic, linoleic, ricinoleic, arachidic, behenic, and erucic acids. Specific examples of fatty alcohols for use as emollients include lauryl, myristyl, cetyl, hexadecyl, stearyl, isostearyl, hydroxystearyl, oleyl, ricinoleyl, behenyl, and erucyl alcohols, as well as 2-octyl dodecanol.

Specific examples of waxes suitable for use as emollients include lanolin and derivatives thereof including lanolin oil, lanolin wax, lanolin alcohols, lanolin fatty acids, isopropyl lanolate, ethoxylated lanolin, ethoxylated lanolin alcohols, ethoxolated cholesterol, propoxylated lanolin alcohols, acetylated lanolin, acetylated lanolin alcohols, lanolin alcohols linoleate, lanolin alcohols recinoleate, acetate of lanolin alcohols recinoleate, acetate of lanolin alcohols recinoleate, acetate of ethoxylated alcohols esters, hydrogenolysates of lanolin, hydrogenated lanolin, ethoxylated hydrogenated lanolin, ethoxylated sorbitol lanolin, and liquid and semi-solid lanolin. Also usable as waxes include hydrocarbon waxes, ester waxes, and amide waxes. Useful waxes include wax esters such as beeswax, spermaceti, myristyl myristate and stearyl stearate; beeswax derivatives, e.g., polyoxyethylene sorbitol beeswax; and vegetable waxes including carnauba and candelilla waxes.

Polyhydric alcohols and polyether derivatives may be used as solvents and/or surfactants in the topical formulations. Suitable polyhydric alcohols and polyethers include propylene glycol, dipropylene glycol, polypropylene glycols 2000 and 4000, poly(oxyethylene-co-oxypropylene) glycols, glycerol, sorbitol, ethoxylated sorbitol, hydroxypropylsorbitol, polyethylene glycols 200-6000, methoxy polyethylene glycols 350, 550, 750, 2000 and 5000, poly[ethylene oxide] homopolymers (100,000-5,000,000), polyalkylene glycols and derivatives, hexylene glycol, 2-methyl-2,4-pentanediol, 1,3-butylene glycol, 1,2,6-hexanetriol, 2-ethyl-1,3-hexanediol, vicinal glycols having 15 to 18 carbon atoms, and polyoxypropylene derivatives of trimethylolpropane.

Polyhydric alcohol esters may be used as emulsifiers or emollients. Suitable polyhydric alcohol esters include ethylene glycol mono- and di-fatty acid esters, diethylene glycol mono- and di-fatty acid esters, polyethylene glycol (200-6000) mono- and di-fatty acid esters, propylene glycol mono- and di-fatty esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Suitable emulsifiers for use in topical formulations include anionic, cationic, nonionic, and zwitterionic surfactants. Preferred ionic emulsifiers include phospholipids, such as lecithin and derivatives.

The molecule or a salt or derivative thereof, can be formulated as a liposome. The molecule can be a component of the lipid portion of the liposome or can be encapsulated in the aqueous portion of the liposome. The molecule or a salt or derivative thereof, can also be coformulated with a cyclodextrin. The cyclodextrin can be, for example, hydroxypropyl-β-cyclodextrin or a sulfobutylether cyclodextrin. Lecithin and other phospholipids may be used to prepare liposomes containing active ingredients as described herein. Formation of lipid vesicles occurs when phospholipids such as lecithin are placed in water and consequently form one bilayer or a series of bilayers, each separated by water molecules, once enough energy is supplied. Liposomes can be created by sonicating phospholipids in water. Low shear rates create multilamellar liposomes. Continued high-shear sonication tends to form smaller unilamellar liposomes. Hydrophobic chemicals can be dissolved into the phospholipid bilayer membrane. The lipid bilayers of the liposomes deliver the compositions as described herein.

The topical formulations may contain micelles, or an aggregate of surfactant molecules dispersed in an aqueous solution. Micelles may be prepared by dispersing an oil solvent in an aqueous solution comprising a surfactant, where the surfactant concentration exceeds the critical micelle concentration. The resulting formulation contains micelles, i.e., spherical oil droplets surrounded by a membrane of polar surfactant molecules, dispersed in the aqueous solvent.

Sterols including, for example, cholesterol and cholesterol fatty acid esters; amides such as fatty acid amides, ethoxylated fatty acid amides, and fatty acid alkanolamides may also be used as emollients and/or penetration enhancers.

A pharmaceutically acceptable preservative can be employed to increase the shelf life of the composition. Other suitable preservatives and/or antioxidants for use in topical formulations include benzalkonium chloride, benzyl alcohol, phenol, urea, parabens, butylated hydroxytoluene (BHT), butylated hydroxyanisole (BHA), tocopherol, thimerosal, chlorobutanol, or the like, and mixtures thereof, can be employed. If a preservative, such as an antioxidant, is employed, the concentration is typically from about 0.02% to about 2% based on the total weight of the composition, although larger or smaller amounts can be desirable depending upon the agent selected. Reducing agents, as described herein, can be advantageously used to maintain good shelf life of the formulation. It is generally observed that the anhydrous formulations of the embodiments exhibit satisfactory stability, such that a preservative can be omitted from the formulation.

Suitable chelating agents for use in topical formulations include ethylene diamine tetraacetic acid, alkali metal salts thereof alkaline earth metal salts thereof, ammonium salts thereof, and tetraalkyl ammonium salts thereof.

The carrier preferably has a pH of between about 4.0 and 10.0, more preferably between about 6.8 and about 7.8. The pH may be controlled using buffer solutions or other pH modifying agents. Suitable pH modifying agents include phosphoric acid and/or phosphate salts, citric acid and/or citrate salts, hydroxide salts (i.e., calcium hydroxide, sodium hydroxide, potassium hydroxide) and amines, such as triethanolamine. Suitable buffer solutions include a buffer comprising a solution of monopotassium phosphate and dipotassium phosphate, maintaining a pH of between 5.8 and 8; and a buffer comprising a solution of monosodium phosphate and disodium phosphate, maintaining a pH of between 6 and 7.5. Other buffers include citric acid/sodium citrate, and dibasic sodium phosphate/citric acid. The compositions of the embodiments are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. It can be desirable to include a reducing agent in the formulation, such as vitamin C, vitamin E, or other reducing agents as are known in the pharmaceutical arts.

Surfactants can also be employed as excipients, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

When the formulations of the embodiments are administered by subcutaneous injection, it is preferably in the form of a pyrogen-free, parenterally acceptable aqueous solution or oleaginous suspension, emulsion or solution. Suspensions can be formulated according to methods well known in the art using suitable dispersing or wetting agents and suspending agents. The preparation of acceptable aqueous or non-aqueous solutions with suitable properties, e.g., pH, isotonicity, stability, and the like, is within the skill in the art. For example, an isotonic vehicle such as 1,3-butanediol, water, isotonic sodium chloride solution, Ringer's solution, dextrose solution, dextrose and sodium chloride solution, lactated Ringer's solution, or other vehicles as are known in the art can be employed, or a fixed oil can be employed conventionally as a solvent or suspending medium, e.g., synthetic mono or diglycerides, fatty acids, or the like. The formulations can also contain stabilizers, preservatives, buffers, antioxidants, or other additives known to those of skill in the art.

In certain embodiments, it can be advantageous to include additional agents having pharmacological activity. Anti-infective agents include, but are not limited to, anthelmintic (mebendazole), antibiotics including aminoglycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin, clindamycin, colistimethate sodium, polymyxin b sulfate, vancomycin, antivirals including acyclovir, amantadine, didanosine, efavirenz, foscarnet, ganciclovir, indinavir, lamivudine, nelfinavir, ritonavir, saquinavir, stavudine, valacyclovir, valganciclovir, zidovudine, quinolones (ciprofloxacin, levofloxacin), sulfonamides (sulfadiazine, sulfisoxazole), sulfones (dapsone), furazolidone, metronidazole, pentamidine, sulfanilamidum crystallinum, gatifloxacin, and sulfamethoxazole/trimethoprim. Anesthetics can include, but are not limited to, ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and phenazopyridine. Anti-inflammatory agents include but are not limited to, nonsteroidal anti-inflammatory drugs (NSAIDs) such as aspirin, celecoxib, choline magnesium trisalicylate, diclofenac potassium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinonide, betamethasone dipropionate, betamethasone valerate, desonide, desoximetasone, fluocinolone, triamcinolone, clobetasol propionate, and dexamethasone.

In certain embodiments, the addition of emollients, emulsion stabilizers, moisturizers, excipients, and other compounds may be modified to enhance the sensory properties of the topical compositions, including but not limited to: skin feel (silkiness, lightness, creaminess, etc.), absorbency (required time at which product loses wet feel and is no longer perceived on skin), consistency, firmness, spread ability (e.g. viscosity, flow onset, shear rates), stickiness, integrity of shape, glossiness, hydrophilicity or hydrophobicity, and others.

In certain embodiments systemic administration of a molecule of the embodiments or a salt or derivative thereof, can be desirable. In such embodiments, the molecule is formulated into a composition suitable for oral administration, but other routes of administration are also contemplated.

The compositions described herein can be administered by themselves to a subject, or in compositions where they are mixed with other active agents, as in combination therapy, or with carriers, diluents, excipients or combinations thereof. Formulation is dependent upon the route of administration chosen. Techniques for formulation and administration of the compounds described herein are known to those skilled in the art (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

The compositions disclosed herein may be manufactured into administrable forms by a process that is itself known, e.g., by means of conventional mixing, dissolving, granulating, dragee-making, levigating, emulsifying, encapsulating, entrapping, tableting, or extracting processes. Many of the compounds used in the pharmaceutical combinations disclosed herein may be provided as salts with pharmaceutically acceptable counterions.

Multiple techniques of administering a molecule of the embodiments exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Contemplated herein is any combination of the forgoing, or other methods as would be known to one of ordinary skill in the art. See, e.g., "Remington: The Science and Practice of Pharmacy", Lippincott Williams & Wilkins, 20th edition (Jun. 1, 2003). See also "Remington's Pharmaceutical Sciences," Mack Pub. Co., 18th and 19th editions (December 1985, and June 1990, respectively).

In practice, the molecule may be combined as the active ingredient in intimate admixture with a pharmaceutical carrier according to conventional pharmaceutical compounding techniques. The molecule can be added directly to, e.g., a gelatin capsule or a soft gel capsule for consumption by the patient. In other embodiments, carriers can be employed. The carrier can take a wide variety of forms depending on the form of preparation desired for administration. Thus, the compositions provided herein can be presented as discrete units suitable for oral administration such as capsules, cachets or tablets each containing a predetermined amount of the active ingredient. Further, the compositions can be presented as an oil, a powder, as granules, as a solution, as a suspension in an aqueous liquid, as a non-aqueous liquid, as an oil-in-water emulsion, or as a water-in-oil liquid emulsion, similar to the topical formulations described elsewhere herein, but using components suitable for human consumption. In addition to the common dosage forms set out above, the compositions provided herein can also be administered by controlled release and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredients with liquid carriers or finely divided solid carriers or both. The product can then be conveniently shaped into the desired presentation.

A formulation may also be administered in a local rather than systemic manner, for example, via injection of the composition directly into a target area, e.g., in a depot or sustained release formulation. Furthermore, a targeted drug delivery system for the composition may be used, for example, in a liposome coated with a tissue specific antibody.

The compositions may contain the molecule of the embodiments in an amount effective for the desired therapeutic effect. In some embodiments, the compositions are in a unit dosage form and comprise from about 0.1 mg or less to about 5000 mg or more of the molecule per unit dosage form. In further embodiments, the compositions comprise from about 1 to about 500 mg per unit dosage form or from about 500 to 5000 mg per unit dosage form of the molecule. Such dosage forms may be solid, semisolid, liquid, an emulsion, or adapted for delivery via aerosol or the like for inhalation administration.

The carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, lower alcohols, and water. Examples of gaseous carriers include carbon dioxide and nitrogen.

The compositions provided herein can be prepared as solutions or suspensions of the molecule of the embodiments in water or nonaqueous liquids. A suitable surfactant can be included such as, for example, hydroxypropylcellulose. Dispersions can also be prepared in glycerol, liquid polyethylene glycols, and mixtures thereof in oils. Further, a preservative can be included to, for example, prevent the detrimental growth of microorganisms.

Compositions provided herein suitable for injectable use include sterile aqueous solutions or dispersions. Furthermore, the compositions can be in the form of sterile powders for the extemporaneous preparation of such sterile injectable solutions or dispersions. The compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

In addition to the aforementioned carrier ingredients, the formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood or other bodily fluids of the intended recipient. Compositions containing a compound provided herein, or pharmaceutically acceptable salt or derivative thereof, can also be prepared in powder or liquid concentrate form for dilution.

Contemplated herein are compositions including the molecule of the embodiments in combination with at least one additional active agent. The molecule of the embodiments and the at least one additional active agent(s) may be present in a single formulation or in multiple formulations provided together, or may be unformulated. In some embodiments, the molecule of the embodiments can be administered with one or more additional agents together in a single composition. For example, the molecule of the embodiments can be administered in one composition, and at least one of the additional agents can be administered in a second composition. In a further embodiment, the molecule of the embodiments and the at least one additional active agent(s) are co-packaged in a kit. For example, a drug manufacturer, a drug reseller, a physician, a compounding shop, or a pharmacist can provide a kit comprising the molecule of the embodiments in combination with another product or component for delivery to a patient. Such additional components can include anti-infective agents, anti-inflammatory agents, anesthetics, or the like.

Some embodiments described herein relate to oral compositions of molecule of the embodiments, which can include a therapeutically effective amount of the molecule of the embodiments described herein and a pharmaceutically acceptable carrier, diluent, excipient or combination thereof. The compositions can include the molecule of the embodiments in an amount for example, >1%, ≥2%, ≥3%, ≥4%, ≥5%, ≥6%, ≥7%, ≥8%, ≥9%, ≥10%, ≥20%, ≥30%, ≥40%, ≥50%, ≥60%, ≥70%, ≥80%, ≥90%, ≥95%, or ≥98% of the composition. In some embodiments, the pharmaceutical composition can include a plurality of small molecule metabolites, such as one or more of an amino acid, peptide, carbohydrate, cofactor, vitamins, xenobiotic, and/or lipid described herein, or salts or derivatives thereof in, for example, >1%, ≥2%, ≥3%, ≥4%, ≥5%, ≥6%, ≥7%, ≥8%, ≥9%, ≥10%, ≥20%, ≥30%, ≥40%, ≥50%, ≥60%, ≥70%, ≥80%, ≥90%, ≥95%, or ≥98% of the composition.

Foodstuffs

Foodstuffs and other comestibles including a monohydroxy fatty acid, such as 2-hydroxymyristate, or a histadine metabolism intermediate, such as N-acetylhistamine described herein, or a salt or derivative thereof, are provided, wherein an amount of the small molecule metabolite in the foodstuff has been fortified (e.g., enriched or concentrated). A small molecule metabolite, such as an amino acid, carbohydrate, lipid, nucleotide, peptide, or xenobiotic, provided herein may be added to foodstuffs for consumption by a subject. The small molecule metabolite, such as an amino acid, carbohydrate, lipid, nucleotide, peptide, or xenobiotic described herein, may be integrated into one or more ingredients of a foodstuff. The small molecule metabolite, such as an amino acid, carbohydrate, lipid, nucleotide, peptide, or xenobiotic described herein, may be prepared as an ingredient, or may be unprepared. The compound, or preparation including the compound, may be added prior to preparation, during preparation, or following preparation. Preparation may without limitation include cooking, mixing, flavoring, seasoning, blending, boiling, frying, baking, or other processes known in the art. Fortification is preferably at a level so as to provide a therapeutic daily dosage of the small molecule metabolite as described elsewhere herein; however, beneficial effects may also be obtained at amounts below such dosages.

A monohydroxy fatty acid, such as 2-hydroxymyristate, or a histadine metabolism intermediate, such as N-acetylhistamine, or salt or derivative thereof, as provided herein may be present as a constituency in foodstuffs by operation of processes known in nature, for example, by altering the metabolic processes of a plant, animal, bacteria, or fungus. Genetic alteration of a plant, animal, bacteria, or fungus to increase the concentration of a monohydroxy fatty acid, such as 2-hydroxymyristate, or a histadine metabolism intermediate, such as N-acetylhistamine as described herein, or a salt or derivative thereof, is contemplated. By way of example, the small molecule metabolite can be present in the foodstuff in a concentration of at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, or higher, for example, 1% to 2% or 3% or 4% or 5% or 6% or 7% or 8% or 9% or 10% or 20% or 30% or 40% or 50%. The small molecule metabolite, if naturally present in a foodstuff, can be present in an enriched amount above that which is naturally occurring for the foodstuff, e.g., a concentration of 10% or more above the average or highest naturally occurring observed concentration, e.g., 20% or 30% or 40% or 50% or 100% or 200% or 300% or 400% or 1000% or 2000% or 5000% or more above the average or highest naturally occurring observed concentration.

Indications

Provided are compositions and methods for treating neuromuscular disorders, including muscular dystrophies (such as Duchenne muscular dystrophy, Becker's muscular dystrophy, congenital muscular dystrophy, distal muscular dystrophy, Emery-Dreifuss muscular dystrophy, fascioscapulohumeral muscular dystrophy, limb-girdle muscular dystrophy, myotonic dystrophy including myotonic dystrophy type 1 and myotonic dystrophy type 2, and oculopharyngeal muscular dystrophy), peripheral motor neuron diseases and motor neuron diseases (such as amyotrophic lateral sclerosis, progressive bulbar palsy, pseudobulbar palsy, progressive muscular atrophy, primary lateral sclerosis, and monomelic amyotrophy), neuromuscular junction diseases (such as myasthenia gravis, congenital myasthenic syndrome, Lambert-Eaton myasthenia syndrome, neuromyotonia and botulism), myopathies (such as mitochondrial myopathies, nemaline myopathy, myotubular myoapathies, familial periodic paralysis), inflammatory muscle disorders (including but not limited to polymyalgia rheumatic, polymositis, and rhabomyolysis), metabolic diseases of the muscle (such as glycogen storage diseases and lipid storage disorders), cardiomyopathies (such as acute myocarditis, dilated cardiomyopathy, obstructive hypertrophy cardiomyopathy, endomyocardial (eosinophilic) disease, endocardial fibrosis, endocardial fibroelastosis, other restrictive cardiomyopathies, alcoholic cardiomyopathy, and other cardiomyopathies), Parkinson's disease, motor neuron diseases, Huntington's disease, Cruetzfeldt-Jakob disease, spinocerebellar ataxia, spinal muscular atrophy, and multiple sclerosis and related conditions, including but not limited to autoimmune disorders, genetic or hereditary disorders, collagen disorders such as Ehlers-Danlos Syndrome, tetanus, and tumors (including but not limited to leimyoma and rhabdomyoma).

Neuromuscular disorder refers to a chronic, progressive condition that affects nerves that control voluntary muscles and the nerves that communicate sensory information back to the brain and results in muscle loss, muscle weakness, movement issues, trouble swallowing and trouble breathing. Autoimmune diseases, gene mutations, inherited conditions, fibrosis, and low miR-29c levels contribute to the onset and progression of neuromuscular diseases due to direct and indirect damage to muscles.

In some embodiments, the compositions and methods provided herein are indicated for treatment, prophylaxis, prevention or maintenance of neuromuscular disorders, including muscular dystrophies, peripheral motor neuron diseases, motor neuron diseases, neuromuscular junction diseases, myopathies, metabolic diseases of the muscle, Parkinson's disease, and amyotrophic lateral sclerosis and associated conditions, including fibrosis.

In some embodiments, the methods provided herein increase levels of serum, plasma, or erythrocyte membrane monohydroxy fatty acids.

In some embodiments, the methods provided herein increase levels of serum, plasma, or erythrocyte membrane histadine metabolism intermediates.

In some embodiments, the compositions and methods provided herein modulate a marker of neuromuscular disorders and associated conditions. In certain embodiments, the marker is serum, plasma, or red blood cell membrane monohydroxy fatty acid or histadine metabolism intermediate percentage; serum, plasma, or red blood cell membrane concentration of a monohydroxy fatty acid or histadine metabolism intermediate; or serum plasma, or red blood cell membrane total monohydroxy fatty acid or histadine metabolism intermediate contained herein.

In some embodiments, the methods provided herein include the step of measuring the concentration of a marker of fibrosis. One of skill in the art will be able to perform suitable methods for such measurements, including but not limited to those described herein.

Provided herein are methods for treating including the step of administering a dose of a monohydroxy fatty acid or histadine metabolism intermediate provided herein, at a predetermined interval, or at an interval left to the discretion of the subject.

In some embodiments, the compounds and methods provided herein may provide a threshold serum, plasma, or red blood cell membrane percentage of a monohydroxy fatty acid or histadine metabolism intermediate relative to all serum, plasma, or red blood cell membrane small molecule biochemicals, respectively. For example, the threshold value may be a value of about 0.05% or lower to 90% or higher, e.g., a value of at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.1%, at least about 1.2%, at least about 1.3%, at least about 1.4%, at least about 1.5%, at least about 1.6%, at least about 1.7%, at least about 1.8%, at least about 1.9%, at least about 2.1%, at least about 2.2%, at least about 2.3%, at least about 2.4%, at least about 2.5%, at least about 2.6%, at least about 2.7%, at least about 2.8%, at least about 2.9%, at least about 3.0%, at least about 3.5%, at least about 4.0%, at least about 4.5%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or more than 90%.

In some embodiments, the compounds and methods provided herein may provide an increase above a baseline value (e.g., pretreatment value in a patient being treated, or general value observed in a particular patient population) in a serum or plasma concentration of a small molecule biochemical, or red blood cell membrane concentration of a monohydroxy fatty acid or histadine metabolism intermediate. For example, a serum or plasma monohydroxy fatty acid or histadine metabolism intermediate or red blood cell membrane concentration of a monohydroxy fatty acid or histadine metabolism intermediate may be increased by at least about 1 µg/ml, at least about 2 µg/ml, at least about 3 µg/ml, at least about 4 µg/ml, at least about 5 µg/ml, at least about 6 µg/ml, at least about 7 µg/ml, at least about 8 µg/ml, at least about 9 µg/ml, at least about 10 µg/ml, at least about 15 µg/ml, at least about 20 µg/ml, at least about 25 µg/ml, at least about 30 µg/ml, at least about 35 µg/ml, at least about 40 µg/ml, at least about 45 µg/ml, at least about 50 µg/ml, or more than 50 µg/ml. In some embodiments, the serum concentration of a monohydroxy fatty acid or histadine metabolism intermediate, or red blood cell membrane concentration of a monohydroxy fatty acid or histadine metabolism intermediate metabolite may increase above a baseline value (e.g., pretreatment value in a patient being treated, or general value observed in a particular patient population) by at least about $0.01 \times 10^{-4}$ M, at least about $0.05 \times 10^{-4}$ M, at least about $0.1 \times 10^{-4}$ M, at least about $0.2 \times 10^{-4}$ M, at least about $0.3 \times 10^{-4}$ M, at least about $0.4 \times 10^{-4}$ M, at least about $0.5 \times 10^{-4}$ M, at least about $0.6 \times 10^{-4}$ M, at least about $0.7 \times 10^{-4}$ M, at least about $0.8 \times 10^{-4}$ M, at least about $0.9 \times 10^{-4}$ M, at least about $1 \times 10^{-4}$ M, at least about $2 \times 10^{-4}$ M, or at least about $3 \times 10^{-4}$ M.

In some embodiments, the compounds and methods provided herein may provide an increase in serum or plasma total monohydroxy fatty acids or histadine metabolism intermediates, or red blood cell membrane total small molecule biochemicals. For example, serum total monohydroxy fatty acids or histadine metabolism intermediates, or red blood cell membrane total monohydroxy fatty acids or histadine metabolism intermediates, may be increased above a baseline value (e.g., pretreatment value in a patient being treated, or general value observed in a particular patient population) by at least about 5 µg/ml, at least about 6 µg/ml, at least about 7 µg/ml, at least about 8 µg/ml, at least about 9 µg/ml, at least about 10 µg/ml, at least about 15 µg/ml, at least about 20 µg/ml, at least about 25 µg/ml, at least about 30 µg/ml, at least about 35 µg/ml, at least about 40 µg/ml, at least about 45 µg/ml, at least about 50 µg/ml, at least about 60 µg/ml, at least about 70 µg/ml, at least about 80 µg/ml, at least about 90 µg/ml, at least about 100 µg/ml, at least about 150 µg/ml, at least about 200 µg/ml, at least about 250 µg/ml, at least about 300 µg/ml, at least about 350 µg/ml, at least about 400 µg/ml, at least about 450 µg/ml, at least about 500 µg/ml, or more than 500 µg/ml.

In some embodiments, the compounds and methods provided herein may provide an increase above a baseline value (e.g., pretreatment value in a patient being treated, or general value observed in a particular patient population) in a serum, plasma, or red blood cell membrane monohydroxy fatty acid or histadine metabolism intermediate relative to all serum or red blood cell membrane small molecule biochemicals, respectively. For example, a serum, plasma, or red blood cell membrane monohydroxy fatty acid or histadine metabolism intermediate may be increased above a baseline value (e.g., pretreatment value in a patient being treated, or general value observed in a particular patient population) by at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.1%, at least about 1.2%, at least about 1.3%, at least about 1.4%, at least about 1.5%, at least about 1.6%, at least about 1.7%, at least about 1.8%, at least about 1.9%, at least about 2%, at least about 2.1%, at least about 2.2%, at least about 2.3%, at least about 2.4%, at least about 2.5%, at least about 2.6%, at least about 2.7%, at least about 2.8%, at least about 2.9%, at least about 3%, at least about 3.5%, at least about 4%, at least about 4.5%, at least about 5%, or more than 5%.

In some embodiments, the compounds and methods provided herein may provide an increase in low miR-29c.

In some embodiments, the compounds and methods provided herein may provide a reduction in fibrosis.

In some embodiments, a monohydroxy fatty acid or histadine metabolism intermediate is administered to maintain serum or plasma total percent of the a monohydroxy fatty acid or histadine metabolism intermediate, or all a monohydroxy fatty acids or histadine metabolism intermediates, above a predetermined threshold value. In variations of these embodiments, the monohydroxy fatty acid is administered to maintain serum phospholipid percent of the small molecule biochemicals, or all small molecule biochemicals, above about 0.1%, about 0.2%, about 0.3%, about 0.4%, about 0.5%, about 0.6%, about 0.7%, about 0.8%, about 0.9%, about 1%, about 1.2%, about 1.4%, about 1.6%, about 1.8%, about 2%, about 2.2%, about 2.4%, or about 2.6%.

In some embodiments, the compounds and methods provided herein may provide a threshold serum, plasma, or red blood cell membrane percentage of a monohydroxy fatty acid or histadine metabolism intermediate relative to all serum or red blood cell membrane small molecule biochemicals, respectively. For example, the threshold value may be a value of about 0.05% or lower to 90% or higher, e.g., a value of at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.1%, at least about 1.2%, at least about 1.3%, at least about 1.4%, at least about 1.5%, at least about 1.6%, at least about 1.7%, at least about 1.8%, at least about 1.9%, at least about 2.1%, at least about 2.2%, at least about 2.3%, at least about 2.4%, at least about 2.5%, at least about 2.6%, at least about 2.7%, at least about 2.8%, at least about 2.9%, at least about 3.0%, at least about 3.5%, at least about 4.0%, at least about 4.5%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or more than 90%.

In some embodiments, the compounds and methods provided herein may provide an increase above a baseline value (e.g., pretreatment value in a patient being treated, or general value observed in a particular patient population) in a serum or plasma concentration of a monohydroxy fatty acid or histadine metabolism intermediate, or red blood cell membrane concentration of a monohydroxy fatty acid or histadine metabolism intermediate. For example, a serum monohydroxy fatty acid or histadine metabolism intermediate or red blood cell membrane concentration of a monohydroxy fatty acid or histadine metabolism intermediate may be increased by at least about 0.01 μg/ml, at least about 0.05 μg/ml, at least about 0.1 μg/ml, at least about 0.4 μg/ml, 1 μg/ml, at least about 2 μg/ml, at least about 3 μg/ml, at least about 4 μg/ml, at least about 5 μg/ml, at least about 6 μg/ml, at least about 7 μg/ml, at least about 8 μg/ml, at least about 9 μg/ml, at least about 10 μg/ml, at least about 15 μg/ml, at least about 20 μg/ml, at least about 25 μg/ml, at least about 30 μg/ml, at least about 35 μg/ml, at least about 40 μg/ml, at least about 45 μg/ml, at least about 50 μg/ml, or more than 50 μg/ml. In some embodiments, the serum concentration of monohydroxy fatty acid or histadine metabolism intermediate, or red blood cell membrane concentration of a monohydroxy fatty acid or histadine metabolism intermediate may increase above a baseline value (e.g., pretreatment value in a patient being treated, or general value observed in a particular patient population) by at least about $0.001 \times 10^{-4}$ M, at least about $0.005 \times 10^{-4}$ M, at least about $0.05 \times 10^{-4}$ M, at least about $0.01 \times 10^{-4}$ M, at least about $0.05 \times 10^{-4}$ M, at least about $0.1 \times 10^{-4}$ M, at least about $0.2 \times 10^{-4}$ M, at least about $0.3 \times 10^{-4}$ M, at least about $0.4 \times 10^{-4}$ M, at least about $0.5 \times 10^{-4}$ M, at least about $0.6 \times 10^{-4}$ M, at least about $0.7 \times 10^{-4}$ M, at least about $0.8 \times 10^{-4}$ M, at least about $0.9 \times 10^{-4}$ M, at least about $1 \times 10^{-4}$ M, at least about $2 \times 10^{-4}$ M, or at least about $3 \times 10^{-4}$ M.

In some embodiments, the compounds and methods provided herein may provide an increase in serum or plasma total monohydroxy fatty acids or histadine metabolism intermediates, or red blood cell membrane total monohydroxy fatty acids or histadine metabolism intermediates. For example, serum total monohydroxy fatty acids or histadine metabolism intermediates, or red blood cell membrane total monohydroxy fatty acids or histadine metabolism intermediates, may be increased above a baseline value (e.g., pretreatment value in a patient being treated, or general value observed in a particular patient population) by at least about 0.05 μg/ml, at least about 0.1 μg/ml, at least about 0.5 μg/ml, at least about 1 μg/ml, at least about 5 μg/ml, at least about 6 μg/ml, at least about 7 μg/ml, at least about 8 μg/ml, at least about 9 μg/ml, at least about 10 μg/ml, at least about 15 μg/ml, at least about 20 μg/ml, at least about 25 μg/ml, at least about 30 μg/ml, at least about 35 μg/ml, at least about 40 μg/ml, at least about 45 μg/ml, at least about 50 μg/ml, at least about 60 μg/ml, at least about 70 μg/ml, at least about 80 μg/ml, at least about 90 μg/ml, at least about 100 μg/ml, at least about 150 μg/ml, at least about 200 μg/ml, at least about 250 μg/ml, at least about 300 μg/ml, at least about 350 μg/ml, at least about 400 μg/ml, at least about 450 μg/ml, at least about 500 μg/ml, or more than 500 μg/ml.

Combination Therapies

In some embodiments, the compounds disclosed herein, such as a monohydroxy fatty acid or histadine metabolism intermediate, or a salt or derivative thereof, or a pharmaceutical composition that includes a compound described herein, or a salt or derivative thereof, may be used in combination with one or more additional active agents. Examples of additional active agents that can be used in combination with a compound of a monohydroxy fatty acid or histadine metabolism intermediate metabolite, or a salt or derivative thereof, or a composition that includes a compound of a monohydroxy fatty acid or histadine metabolism intermediate, or a salt or derivative thereof, include, but are not limited to, agents currently used for treating conditions provided herein, and as otherwise known to medical science.

In some embodiments, a compound of monohydroxy fatty acid or histadine metabolism intermediate, or a salt or derivative thereof, or a composition that includes a compound of a monohydroxy fatty acid or histadine metabolism intermediate, or a salt or derivative thereof, can be used with one, two, three or more additional active agents described herein. Such agents include, but are not limited to, a second monohydroxy fatty acid or histadine metabolism intermediate, or a salt or derivative thereof.

In some embodiments, a compound of a monohydroxy fatty acid or histadine metabolism intermediate, or a salt or derivative thereof, or a composition that includes a compound of a monohydroxy fatty acid or histadine metabolism intermediate described herein, or a salt or derivative thereof, can be used (for example, administered or ingested) in combination with another agent or agents for treatment, prevention, maintenance, or prophylaxis of a condition provided herein including muscular dystrophies (for example, Duchenne muscular dystrophy, Becker's muscular dystrophy, congenital muscular dystrophy, distal muscular dystrophy, Emery-Dreifuss muscular dystrophy, fascioscapulohumeral muscular dystrophy, limb-girdle muscular dystrophy, myotonic dystrophy including myotonic dystrophy type 1 and myotonic dystrophy type 2, or oculopharyngeal muscular dystrophy), peripheral motor neuron diseases and motor neuron diseases (for example, amyotrophic lateral sclerosis, progressive bulbar palsy, pseudobulbar palsy, progressive muscular atrophy, primary lateral sclerosis, or monomelic amyotrophy), neuromuscular junction diseases (for example, myasthenia gravis, congenital myasthenic syndrome, Lambert-Eaton myasthenia syndrome, neuromyotonia or botulism), myopathies (for example, mitochondrial myopathies, nemaline myopathy, myotubular myoapathies, familial periodic paralysis), inflammatory muscle disorders (for example, polymyalgia rheumatic, polymositis, and rhabomyolysis), metabolic diseases of the muscle (for example, glycogen storage diseases and lipid storage disorders), cardiomyopathies (for example, acute myocarditis, dilated cardiomyopathy, obstructive hypertrophy cardiomyopathy, endomyocardial (eosinophilic) disease, endocardial fibrosis, endocardial fibroelastosis, other restrictive cardiomyopathies, alcoholic cardiomyopathy, and other cardiomyopathies), Parkinson's disease, prion disease, motor neuron diseases, Huntington's disease, Cruetzfeldt-Jakob disease, spinocerebellar ataxia, spinal muscular atrophy, and multiple sclerosis and related conditions to neuromuscular disorders, including but not limited to autoimmune disorders, genetic or hereditary disorders, collagen disorders such as Ehlers-Danlos Syndrome, tetanus, and tumors (for example, leimyoma and rhabdomyoma). For example, a monohydroxy fatty acid or histadine metabolism intermediate, such as a monohydroxy fatty acid or histadine metabolism intermediate disclosed herein, can be used in combination with one or more agents selected from iron chelators, albiglutide, aleglitazar, balaglitazone, canagliflozin, CJ-30001 (CJ Cheiljedang Corporation), CJ-30002 (CJ Cheiljedang Corporation), Diamyd® (glutamic acid decarboxylase (rhGAD65)), dulaglutide, exendin 4, gemigliptin, lixisenatide, lobeglitazone, shengke I (Tibet Pharmaceuticals), SK-0403 (Sanwa Kagaku Kenkyusho), teneligliptin, teplizumab, tofogliflozin, acarbose, alogliptin benzoate, chlorpropamide, Diab II (Biotech Holdings), exenatide, glibenclamide, gliclazide, glimepiride, glipizide, gliquidone, glisentide, glisolamide, HL-002 (HanAII Biopharma), insulin (human), insulin, insulin analogue (Eli Lilly®), insulin aspart, insulin detemir, insulin glargine, insulin lispro, Janumet®, linagliptin, liraglutide, metformin, miglitol, mitiglinide, nateglinide, Novo Mix 30® (Novo Nordisk®) pioglitazone, pramlintide, repaglinide, rosiglitazone maleate, saxagliptin, sitagliptin, Tresiba, tolazamide, tolbutamide, vildagliptin, voglibose, bezafibrate, diflunisal, cinnamic acid, carbutamide, glyburide (glibenclamide), glibomuride, glyhexamide, phenbutamide, and tolcyclamide or with one or more agents selected from a class of agents, where the classes include sulfonylureas, non-sulfonylurea secretagogues, glucagon-like peptides, exendin-4 polypeptides, beta 3 adrenoceptor agonists, PPAR agonists, dipeptidyl peptidase IV inhibitors, biguanides, alpha-glucosidase inhibitors, immunomodulators, statins and statin-containing combinations, angiotensin converting enzyme inhibitors, adeno sine A1 receptor agonists, adenosine A2 receptor agonists, aldosterone antagonists, alpha 1 adrenoceptor antagonists, alpha 2 adrenoceptor agonists, alpha 2 adrenoceptor agonists, angiotensin receptor antagonists, antioxidants, ATPase inhibitors, atrial peptide agonists, beta adrenoceptor antagonists, calcium channel agonists, calcium channel antagonists, diguanides, diuretics, dopamine D1 receptor agonists, endopeptidase inhibitors, endothelin receptor antagonists, guanylate cyclase stimulants, phosphodiderivativease V inhibitors, protein kinase inhibitors, Cdc2 kinase inhibitors, renin inhibitors, thromboxane synthase inhibitors, vasopeptidase inhibitors, vasopressin I antagonists, vasopressin 2 antagonists, angiogenesis inhibitors, advanced glycation end product inhibitors, bile acid binding agents, bile acid transport inhibitors, bone formation stimulants, apolipoprotein A1 agonists, DNA topoisomerase inhibitors, cholesterol absorption inhibitors, cholesterol antagonists, cholderivativeyl derivative transfer protein antagonists, cytokine synthesis inhibitors, DNA polymerase inhibitors, dopamine D2 receptor agonists, endothelin receptor antagonists, growth hormone antagonists, insulin sensitizers, lipase inhibitors, lipid peroxidation inhibitors, lipoprotein A antagonists, microsomal transport protein inhibitors, microsomal triglyceride transfer protein inhibitors, nitric oxide synthase inhibitors, oxidizing agents, phospholipase A2 inhibitors, radical formation agonists, platelet aggregation antagonists, prostaglandin synthase stimulants, reverse cholesterol transport activators, rho kinase inhibitors, selective estrogen receptor modulators, squalene epoxidase inhibitors, squalene synthase inhibitors, thromboxane A2 antagonists, amylin agonists, cannabinoid receptor antagonists, cholecystokinin A agonists, corticotropin-releasing factor agonists, dopamine uptake inhibitors, G protein-coupled receptor modulators, glutamate antagonists, glucagon-like peptide-1 agonists lipase inhibitors, melanin-concentrating hormone receptor antagonists, nerve growth factor agonists, neuropeptide Y agonists, neuropeptide Y antagonists, SNRIs, protein tyrosine phosphatase inhibitors, serotonin 2C receptor agonists, or with other agents such as central nervous system agents that affect neurotransmitters or neural ion channels, including antidepressants (bupropion), noradrenalin reuptake inhibitors (GW320659), selective serotonin 2c receptor agonists, selective 5HT 2c receptor agonists, antiseizure agents (topiramate, zonisamide), dopamine antagonists, cannabinoid-1 receptor antagonists (CB-1 receptor antagonists) (rimonabant); leptin/insulin/central nervous system pathway agents, including leptin analogues, leptin transport and/or leptin receptor promoters, ciliary neurotrophic factor (Axokine), neuropeptide Y and agouti-related peptide antagonists, pro-opiomelanocortin and cocaine and amphetamine regulated transcript promoters, α-melanocyte-stimulating hormone analogues, melanocoritin-4 receptor agonists, and agents that affect insulin metabolism/activity, which include protein-tyrosine phosphatase-IB inhibitors, peroxisome proliferator activated receptor-.gamma. receptor antagonists, short-acting bromocriptine (ergoset), somatostatin agonists (octreotide), and adiponectin/Acrp30 (Famoxin or Small molecule metabolite Metabolic Oxidation Inducer); gastrointestinal-neural pathway agents, including those that increase cholecystokinin activity (CCK), PYY activity, NPY activity, and PP activity, increase glucagon-like peptide-1 activity (exendin 4, dipeptidyl peptidase IV inhibitors), and those that decrease ghrelin activity, as well as amylin analogues (pramlintide); agents that may increase resting metabolic rate (selective β-3 stimulators/agonist, uncoupling protein homologues, and thyroid receptor agonists); other more diverse agents, including melanin concentrating hormone antagonists, phytostanol analogues, functional oils, P57, amylase inhibitors, growth hormone fragments, synthetic analogues of dehydroepiandrosterone sulfate, antagonists of adipocyte 11B-hydroxysteroid dehydrogenase type 1 activity, corticotropin-releasing hormone agonists, inhibitors of small molecule metabolite synthesis (cerulenin and C75), carboxypeptidase inhibitors, indanone/indanols, aminosterols (trodusquemine/trodulamine), and other gastrointestinal lipase inhibitors (ATL962); amphetamines, such as dextroamphetamine; other sympathomimetic adrenergic agents, including phentermine, benzphetamine, phendimetrazine, mazindol, and diethylpropion; or with one or more agents selected from ecopipam; oxyntomodulin (OM); inhibitors of glucose-dependent insulinotropic polypeptide (GIP); gastrin-releasing peptide; neuromedin B; enterostatin; amfebutamone, SR-58611; CP-045598; AOD-0604; QC-BT16; rGLP-1; 1426 (HMR-1426); N-5984; ISIS-1 13715; solabegron; SR-147778; Org-34517; melanotan-II; cetilistat; c-2735; c-5093; c-2624; APD-356; radafaxine; fluasterone; GP-389255; 856464; S-2367; AVE-1625; T-71; oleoyl-estrone; peptide YY [3-36] intranasal; androgen receptor agonists; PYY 3-36; DOV-102677; tagatose; SLV-319; 1954 (Aventis Pharma AG); oxyntomodulin, Thiakis; bromocriptine, PLIVA; diabetes/hyperlipidemia therapy, Yissum; CKD-502; thyroid receptor beta agonists; beta-3 adrenoceptor agonist; CDK-A agonists; galanin antagonist; dopamine D1 D2 agonists; melanocortin modulators; verongamine; neuropeptide Y antagonists; melanin-concentrating hormone receptor antagonists; dual PPAR alpha/gamma agonists; CGEN-P-4; kinase inhibitors; human MCH receptor antagonists; GHS-R antagonists; ghrelin receptor agonists; DG70 inhibitors; cotinine; CRF-BP inhibitors; urocortin agonists; UCL-2000; impentamine; β-3 adrenergic receptor; pentapeptide MC4 agonists; trodusquemine; GT-2016; C-75; CPOP; MCH-1 receptor antagonists; RED-103004; aminosterols; orexin-1 antagonists; neuropeptide Y5 receptor antagonists; DRF-4158; PT-15; PTPase inhibitors; A37215; SA-0204; glycolipid metabolites; MC-4 agonist; produlestan; PTP-1B inhibitors; GT-2394; neuropeptide Y5 antagonists; melanocortin receptor modulators; MLN-4760; PPAR gamma/delta dual agonists; NPY5RA-972; 5-HT2C receptor agonist; neuropeptide Y5 receptor antagonists (phenyl urea analogs); AGRP/MC4 antagonists; neuropeptide Y5 antagonists (benzimidazole); glucocorticoid antagonists; MCHR1 antagonists; Acetyl-CoA carboxylase inhibitors; R-1496; HOB 1 modulators; NOX-B11; peptide YY 3-36 (eligen); 5-HT 1 modulators; pancreatic lipase inhibitors; GRC-1087; CB-1 antagonists; MCH-1 antagonists; LY-448100; bombesin BRS3 agonists; ghrelin antagonists; MC4 antagonists; stearoyl-CoA desaturase modulators; PPAR pan agonists; EP-01492; hormone-sensitive lipase inhibitors; small molecule metabolite-binding protein 4 inhibitors; thiolactone derivatives; protein tyrosine phosphatase IB inhibitors; MCH-1 antagonist; P-64; PPAR gamma ligands; melanin concentrating hormone antagonists; thiazole gastroprokinetics; PA-452; T-226296; A-331440; immunodrug vaccines; diabetes/obesity therapeutics (Bioagency, Biofrontera Discovery GmbH); P-7 (Genfit); DT-011 M; PTP1B inhibitor; anti-diabetic peptide conjugates; KATP agonists; obesity therapeutics (Lexicon); 5-HT2 agonists; MCH-1 receptor antagonists; GMAD-1/GMAD-2; STG-a-MD; angiogenesis inhibitors; G protein-coupled receptor agonists; nicotinic therapeutics (ChemGenex); anti-obesity agents (Abbott); melanin concentrating hormone; GW-594884A; MC-4R agonist; histamine H3 antagonists; orphan GPCR modulators; MITO-3108; NLC-002; HE-2300; IGF/BBP-2-13; 5-HT2C agonists; ML-22952; neuropeptide Y receptor antagonists; AZ-40140; anti-obesity therapy (Nisshin Flour); GNTI; melanocortin receptor modulators; alpha-amylase inhibitors; beta-3 adrenoceptor agonists; ob gene products (Eli Lilly & Co.); SWR-0342-SA; SWR-0335; SP-18904; oral insulin mimetics; obesity therapeutics (7TM Pharma); beta-hydroxysteroid dehydrogenase (HSD) inhibitors; QRX-431; E-6776; RI-450; melanocortin-4 antagonists; melanocortin 4 receptor agonists; obesity therapeutics (CuraGen); leptin mimetics; A-74498; second-generation leptin; NBI-103; CL-314698; CP-114271; beta-3 adrenoceptor agonists; NMI-8739; UCL-1283; BMS-192548; CP-94253; PD-160170; nicotinic agonist; LG-100754; SB-226552; LY-355124; CKD-711; L-751250; PPAR inhibitors; G-protein therapeutics; obesity therapy (Amylin Pharmaceuticals Inc.); BW-1229; monoclonal antibody (ObeSys/CAT); L-742791; (S)-sibutramine; MBU-23; YM-268; BTS-78050; tubby-like protein genes; genomics (eating disorders; Allelix/Lilly); MS-706; GI-264879A; GW-409890; FR-79620 analogs; obesity therapy (Hybrigenics SA); ICI-198157; ESP-A; 5-HT2C agonists; PD-170292; AIT-202; LG-100641; GI-181771; anti-obesity therapeutics (Genzyme); leptin modulator; GHRH mimetics; obesity therapy (Yamanouchi Pharmaceutical Co. Ltd.); SB-251023; CP-331684; BIBO-3304; cholesten-3-ones; LY-362884; BRL-48962; PY-1 antagonists; A-71378; ®-didesmethylsibutramine; obesity therapeutics (Bristol-Myers Squibb Co.); obesity therapeutics (Ligand Pharmaceuticals Inc.); LY-226936; NPY antagonists; CCK-A agonists; FPL-14294; PD-145942; ZA-7114; CL-316243; SR-58878; R-1065; BDBP-3226; HP-228; talibegron; FR-165914; AZM-008; AZM-016; AZM-120; AZM-090; AZM-131; AZM-132; AZM-134; AZM-127; AZM-083; AZM-115; AZM-140; vomeropherin; BMS-187257; D-3800; gene discovery (Axys/Glaxo); BRL-26830A; SX-013; ERR modulators; adipsin; AC-253; A-71623; A-68552; BMS-210285; TAK-677; MPV-1743; obesity therapeutics (Modex); GI-248573; exopipam; SSR-125180; obesity therapeutics (Melacure Therapeutics AB); BRL-35135; SR-146131; P-57; CGP-71583A; RF-1051; BMS-196085; manifaxine; DMNJ (Korea Research Institute of Bioscience and Biotechnology); BVT-5182; LY-255582; SNX-024; galanin antagonists; neurokinin-3 antagonists; dexfenfluramine; mazindol; diethylpropion; phendimetrazine; benzphetamine; amfebutmone; sertraline; AOD-9604; ATL-062; BVT-933; GT389-255; SLV319; HE-2500; PEG-axokine; L-796568; and ABT-239; rimonabant, sibutramine, orlistat, PYY or an analog thereof, CB-1 antagonist, leptin, phentermine, and exendin analogs; GPR1 19 agonists (e.g., anandamide; AR-231, 453; MBX-2982; Oleoylethanolamide; PSN-365,963; PSN-632,408; palmitoylethanolamide); GPR120 agonists; GPR 40 agonists; and SGLT2 inhibitors.

Additionally, a monohydroxy fatty acid or histadine metabolism intermediate or salt or derivative can be used in combination with one or more drugs for treatment of Parkinson's disease, Huntington's disease, and amyotrophic lateral sclerosis. For example, the molecule as provided herein can be used in combination with one or more agents for treatment of diseases selected from cholinesterase inhibitors (Aricept, Exelon, Razadyne) and memantine (Namenda), donepezil, Namenda XR, galatamine, rivastigmine, Aricept ODT, vitamin e, Razadyne ER, Namzaric, donepezil/memantine, Alpha E, Hydergine, ergoloid mesylates, Aqua-E, etanercept, Vita-Plus E Natural, Aqua Gem-E, Aquasol E, Aquavite-E, E-400 Clear, E-600, E-Gems, E Pherol, and Nutr-E-Sol. Anti-amyloid agents, anti-inflammatory agents, Sigma 1 receptor agonists, NMDA receptor antagonists, serotonin norepinephrine reuptake inhibitiors (bupropion), BACE inhibitors, serotonin reuptake inhibitors, insulin, dopamine reuptake inhibitors, orexin receptor antagonists, acetylcholinesterase inhibitors, Tau protein aggregation inhibitors, RAGE antagonists, and/or ositive allosteric modulator of GABA-A receptors can also be employed in combination with the molecules of the embodiments. Additionally, a small molecule metabolite or salt or derivative as provided herein can be used in combination with one or more agents for treatment of Parkinsons disease selected from levodopa, Carbidopa (Lodosyn), Carbidopa-levodopa (Sinemet, Sinemet CR, Parcopa, Rytary) Carbidopa-levodopa-entacopone (Duopa), Entacopone (Comtan), Tolcapone (Tasmar), Carbidopa-levodopa-Entacopone (Stalevo), Pramipexole (Mirapex, Mirapex ER), Ropinirole (Requip, Requip XL), Apomorphine (Apokyn), Rotigotine (Neupro), Selegiline (Zelapar), Rasagiline (Azilect), Safinamide (Xadago), Amantadine (Symmetrel, Gocovri), Trihexyphenidyl (Artane), Baclofen (Lioresal), Dantrolene (Dantrium), Riluzole (Rilutek), Tacrine (Cognex), Tetrabenazine (Xenazinenitoman), Tizandine (Zanaflex), Tolcapone (Tasmar), and Benzotropine (Cogentin). DOPA decarboxylase inhibitors, DA precursors, COMT inhibitors, DA agonist, MAO-B inhibitors, NMDA antagonists, and/or anticholinergics can also be employed in combination with the molecules of the embodiments.

Additionally, a monohydroxy fatty acid or histadine metabolism intermediate or salt or derivative as provided herein can be used in combination with one or more agents selected from Altoprev (lovastatin), Crestor (rosuvastatin), Lescol (fluvastatin), Lipitor (atorvastatin), Livalo (pitavastatin), Pravachol (pravastatin), Zocor (simvastatin), an antiplatelet medication, a beta blocker, an ACE inhibitor, a calcium channel blocker, a diuretic, anticoagulants, aspirin, bile acid sequestrants, Ezetimibe, Fibrates, Glycoprotein IIb/IIIa Receptor Inhibitors, Niacin (Nicotinic Acid), Nitrates, Platelet Inhibitors, Thrombolytics, lisinopril oral, atenolol oral, Bystolic oral, Diovan oral, hydrochlorothiazide oral, metoprolol succinate oral, amlodipine oral, Norvasc oral, Toprol XL oral, Benicar oral, metoprolol tartrate oral, losartan oral, lisinopril-hydrochlorothiazide oral, clonidine HCl oral, Diovan HCT oral, Cozaar oral, propranolol oral, spironolactone oral, Azor oral, carvedilol oral, Coreg oral, Benicar HCT oral, Exforge oral, Avapro oral, Lotrel oral, verapamil oral, furosemide oral, Lasix oral, Hyzaar oral, Tekturna oral, enalapril maleate oral, Micardis oral, losartan-hydrochlorothiazide oral, ramipril oral, Lopressor oral, Altace oral, Micardis HCT oral, Avalide oral, diltiazem oral, triamterene-hydrochlorothiazide oral, labetalol oral, terazosin oral, amlodipine-benazepril oral, hydralazine oral, Atacand oral, benazepril oral, Tribenzor oral, triamterene oral, doxazosin oral, nifedipine oral, Ziac oral, Aldactone oral, Maxzide oral, Cartia XT oral, prazosin oral, Cardizem CD oral, Zestril oral, Dyazide oral, bisoprolol fumarate oral, Tenex oral, Tenormin oral, Coreg CR oral, Prinivil oral, valsartan oral, atenolol-chlorthalidone oral, Edarbyclor oral, benazepril-hydrochlorothiazide oral, ferrous sulfate oral, Ferrlecit intravenous, Feraheme intravenous, Feosol oral, Infed injection, Integra oral, Ferrex 150 Forte oral, Tandem Dual Action oral, Ferrex 150 oral, ferrous gluconate oral, Corvite 150 oral, Integra F oral, NovaFerrum oral, Iron (ferrous sulfate) oral, Vitron-C oral, Folic acid, corticosteroids, rituximab, IVIG, prednisone, methylprednisolone oral, Kenalog injection, Medrol (Pak) oral, Medrol oral, dexamethasone oral, Depo-Medrol injection, prednisolone oral, DexPak 13 Day oral, Solu-Medrol intravenous, hydrocortisone oral, Cortef oral, Deltasone oral, triamcinolone acetonide injection, cortisone oral, cholinesterase inhibitors such as Donepezil (Aricept), Rivastigmine (Exelon), and Galantamine (Razadyne), Memantine, Aricept, Namenda, Namenda XR, Razadyne ER, Alpha E, vitamin E, Hydergine, Namzaric, Dopamine Agonists such as pramipexole (Mirapex), ropinirole (Requip), rotigotine (Neupro patch) and apomorphine (Apokyn), Anticholinergics such as benztropine (Cogentin) and trihexyphenidyl, MAO-B Inhibitors such as (Eldepryl, Zelapar) and rasagiline (Azilect), COMT Inhibitors such as Entacapone (Comtan), Carbidopa/Levodopa (Sinemet®), amantadine, Tetrabenazine (Xenazine), haloperidol (Haldol), chlorpromazine, risperidone (Risperdal), quetiapine (Seroquel), olanzapine (Zyprexa), indomethacin, sulindac, etodolac, mefenamic acid, meclofenamic acid, meclofenamate sodium, flufenamic acid, tolmetin, ketorolac, diclofenac, diclofenac sodium, ibuprofen, naproxen, naproxen sodium, fenoprofen, ketoprofen, flurbiprofen, oxaprozin piroxicam, meloxicam, ampiroxicam, droxicam, lornoxicam, cinnoxicam, sudoxicam, and tenoxicam.

Additionally, a monohydroxy fatty acid or histadine metabolism intermediate or salt or derivative can be used in combination with one or more drugs for treatment of neuromuscular disorders, such as immunosuppressive drugs, including but not limited to corticosteroids (prednisone, budesonide, prednisolone), janus kinase inhibitors (tofacitinib), calcineurin inhibitors (cyclosporine, tacrolimus), mTOR inhibitors (sirolimus, everolimus), IMDH inhibitors (azathioprine, leflunomide, mycophenolate), biologics (abatacept, adalimumab, anakinra, certolizumab, etanercept, golimumab, infliximab, ixekizumab, natalizumab, rituximab, secukinumab, tocilizumab, ustekinumab, vedolizumab), and monoclonal antibodies (basiliximab, daclizumab); anticonvulsants, including but not limited to aldehydes, aromatic allylic alcohols, barbiturates (phenobarbital, methylphenobarbital, barbexaclone), benzodiazepines (clobazam, clonazepam, clorazepate, diazepam, midazolam, lorazepam), bromides (potassium bromide), carboxamides (carbamazepine, oxcarbazepine, eslicarbazepine acetate), fatty acids (valproates, vigabatrin, progabide, tiagabine), fructose derivatives (topiramate), hydantoins (ethotoin, phenytoin, mephenytoin, fosphenytoin), oxazolidinediones (paramethadione, trimethadione, ethdione), propionates (beclamide), pyriminediones (primidone), pyrrolidines (brivaracetam, etiracetam, levetiracetam, seletracetam), succinimides (ethosuximide, phensuximide, mesuximide), sulfonamides (acetazolamide, sultiame, methazolamide, zonisamide), triazenes (lamotrigine), ureas (pheneturide, phenacemide), valproylamides (valpromide, valnoctamide), perampanel, stiripentol, and pyridoxine; and antidepressants, including but not limited to selective serotonin reuptake inhibitors (citalopram, escitalopram, fluoxetine, fluvoxamine, paroxetine, sertraline, vortioxetine, vilazodone), serotonin and norepinephrine reuptake inhibitors (duloxetine, venlafaxine, desvenlafaxine, levomilnacipran), tricylclic antidepressants (amoxapine, amitriptyline, doxepin, trimipramine, desipramine, imipramine, clomipramine, nortriptyline, protriptyline), monoamine oxidase inhibitors, mirtazapine, buprorion, trazodone, vortioxetine, vilazodone, Nusinersen (for the treatment of Spinal Muscular Atrophy, SMA), Eteplirsen (for Duchenne muscular dystrophy), Riluzole for ALS, Mexiletine, modafinil, and armodafinil for myotonic dystrophy type 1.

Dosing

As will be readily apparent to one skilled in the art, the useful in vivo dosage to be administered and the particular mode of administration will vary depending upon the age, weight, the severity of the condition, and mammalian species treated, the particular forms of the compounds employed, and the specific use for which these compounds are employed. The determination of effective dosage levels, that is the dosage levels necessary to achieve the desired result, can be accomplished by one skilled in the art using routine methods, for example, in vivo studies. Reference may be made to, for example, "Estimating the Maximum Safe Starting Dose in Initial Clinical Trials for Therapeutics in Adult Healthy Volunteers," U.S. Food and Drug Administration, July 2005.

In some embodiments, a method provided herein may comprise administering a therapeutically effective amount of a composition provided herein. In some embodiments, a therapeutically effective amount may be determined by reference to the modulation of a marker of a condition provided herein including miR-29c and creatinine. In some embodiments, a therapeutically effective amount may be determined by reference to the modulation of a symptom of a condition provided herein. In still other embodiments, reference may be made to established guidelines for the conditions described herein, including, but not limited to, guidelines for the treatment of a condition provided herein including fibrosis.

The dosage may vary broadly, depending upon the desired effects and the therapeutic indication, such as marker values. Alternatively, dosages may be based and calculated upon the surface area or weight of the patient, as understood by those of skill in the art. The exact dosage will be determined on a case-by-case basis, or, in some cases, will be left to the informed discretion of the subject. The daily dosage regimen for an adult human patient may be, for example, an oral dose of a small molecule metabolite provided herein, or a salt or derivative thereof, or a mixture of a plurality of monohydroxy fatty acids or histadine metabolism intermediates, or a salt or derivative thereof, from about 0.01 mg to about 10000 mg, from about 1 mg to about 5000 mg, from about 5 mg to about 2000 mg, from about 10 mg to about 1000 mg, or from about 50 mg to about 500 mg. A single dose may include a small molecule metabolite, or a salt or derivative thereof, in about 0.01 mg, about 0.1 mg, about 1 mg, about 5 mg, about 10 mg, about 20 mg, about 50 mg, about 100 mg, about 200 mg, about 300 mg, about 400 mg, about 500 mg, about 600 mg, about 800 mg, about 900 mg, about 1000 mg, about 2000 mg, about 5000 mg, or more. The dosage may be adjusted according to the body mass of the subject, for example, the dosage may be about 0.001 mg/kg, about 0.01 mg/kg, about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 15 mg/kg, about 20 mg/kg, about 25 mg/kg, about 30 mg/kg, or higher.

The dosage may be a single one or a series of two or more given in the course of one or more days, as is appropriate for the individual subject. In some embodiments, the compounds will be administered for a period of continuous therapy, for example for about a week or more (e.g., one week, two weeks, three weeks, four weeks, five weeks, six weeks, seven weeks, eight weeks, or more), for several weeks, for about a month or more (e.g., one month, two months, three months, four months, five months, six months, seven months, eight months, nine months, ten months, eleven months, twelve months, or more), for about a year or more, or for a plurality of years. In some embodiments, a monohydroxy fatty acid or histadine metabolism intermediate provided herein, or a salt or derivative thereof, can be administered or ingested one time per day, two times per day, three times per day, or more.

As will be understood by those of skill in the art, in certain situations it may be necessary to administer the compounds disclosed herein in amounts that exceed the above-stated, preferred dosage range in order to effectively treat a subject.

Unit dosage forms can also be provided, e.g., individual packages with a premeasured amount of the composition, configured for administration on a predetermined schedule. Unit dosage forms configured for administration one to three times a day are preferred; however, in certain embodiments it may be desirable to configure the unit dosage form for administration more than three times a day, or less than one time per day.

Dosage amount and interval may be adjusted to the individual subject to provide plasma levels of the active moiety which are sufficient to maintain predetermined parameters, indicators, or marker values, or minimal effective concentration (MEC). Dosages necessary to achieve the desired result will depend on individual characteristics and route of administration. However, assays, for example, HPLC assays or bioassays, may be used to determine serum concentrations.

Diagnosis and Monitoring

Provided herein are methods for the diagnosis and monitoring of conditions provided herein including neuromuscular diseases.

In some embodiments, the method of diagnosis or monitoring may comprise the step of measuring a percentage of a monohydroxy fatty acid, such as 2-hydroxymyristate or histadine metabolism intermediate, such as N-acetylhistamine, as described herein, in a bodily fluid. In some embodiments, the method of diagnosis or monitoring may comprise the step of measuring a marker of a condition provided herein including miR-29c in a subject. In some embodiments, the method of diagnosis or monitoring may comprise the step of measuring a marker of autoimmunity or fibrosis. In some embodiments, a correlation between one marker and another may prove instructive. In some embodiments, a neuromuscular disorder or a related condition may be diagnosed by reference to a threshold level of miR-29c, for example, or serum or plasma monohydroxy fatty acid or histadine metabolism intermediate levels. In some embodiments, a condition provided herein including neuromuscular disorders may be diagnosed by reference to a threshold level of a marker of the condition, for example, serum monohydroxy fatty acid or histadine metabolism intermediate percentage, serum concentration of a monohydroxy fatty acid or histadine metabolism intermediate, or serum total monohydroxy fatty acid or histadine metabolism intermediate, or a ratio between two serum monohydroxy fatty acids or histadine metabolism intermediates. For example, the threshold may be determined by reference to a symptom or marker of a condition provided herein including miR-29c or creatinine. For example, the condition can be muscle atrophy.

The percentage of a monohydroxy fatty acid or histadine metabolism intermediate or a marker of a condition provided herein including miR29c, inflammation, fibrosis, or an autoimmune condition, in a subject may be monitored by any means. Samples for analysis may be derived any fluid or tissue of the subject. For example, from serum, plasma, erythrocyte membranes, urine, and feces.

EXAMPLES

Example 1

Biochemicals (i.e., small molecule biochemicals) present in serum or plasma may serve as biomarkers, therapeutic targets, natural supplements, or therapeutics for neuromuscular disorders. The most promising biochemicals are expected to 1) be detectable in blood, 2) independently predict a biomarker and driver of the condition, and 3) demonstrated ability to be increased in concentration with interventions with correlated and desired changes in the disease biomarker. It was hypothesized that small molecule metabolite biomarkers, therapeutic targets, natural supplements, and therapeutics for neuromuscular diseases could be discovered by identifying biochemicals that met the three criteria above, using samples from bottlenose dolphin populations.

Bottlenose dolphins (*Tursiops truncatus*) are part of the cetacean clade, which includes whales, dolphins, and porpoises. Approximately 53 million years ago, ancestors of dolphins and other cetaceans transitioned from living on land to living in the marine environment (Thewissen et al. 2001). As members of the order Artiodactyla, dolphins and other cetaceans are most closely related to cattle, pigs, and camels. Despite their distant evolutionary relationship to humans, dolphins and humans have unexpected and important similarities related to longevity and aging-associated diseases, including large brain sizes, rapid glucose transport systems, conserved chromosomes, and co-evolved metabolomes and gene regulation to support long lives (Bielec et al. 1998, Venn-Watson et al. 2014).

Human chromosome 1 (hsa1) is the largest of human chromosomes, containing 249 million base pairs and 300 genes (White 2007). Hsa1 is an ancient chromosome that has been entirely conserved in very few other taxa, including great apes and bottlenose dolphins (Murphy et al. 2003). While faster evolutionary rates of other species appear to have resulted in changes to chromosome 1, the relatively slower evolutionary rates of humans, great apes, and dolphins likely explain why these species have conserved hsa1, resulting in the observed ' . . . extraordinary degree of conservation of genome organization [that] has occurred since the divergence of lineages leading to man and dolphin' (Bielec et al. 1998). In humans, hsa1 represents 8% of DNA in cells and more than 148 disease genes, including those related to Alzheimer's disease, hemochromatosis, and hypercholesterolemia. Similar to humans, dolphins are susceptible to developing these diseases, especially with increased age (Gunn-Moore et al. 2018, Venn-Watson et al. 2011, 2012 and 2015).

There are recognized differences in molecular phenotypes when comparing long-lived and short-lived species. This includes distinct amino acid and lipid profiles in the metabolome, proteins and genes related to DNA repair, and lipid components of cell membranes (Ma et al. 2015, Li et al. 2013, Pamplona 2008). Not surprisingly, these adaptations appear to help long-lived species resist environmental stressors better than short-lived species, thus enabling them to live longer. As such, studying metabolomes, gene expression, and cell membranes in long-lived species, including dolphins, can provide novel insight into how to expand longevity. Metabolomics involves the study and measurement of thousands of small molecules present in the body. MicroRNA are small, noncoding RNA that can post-transcriptionally impact gene expression.

Similar genetic, molecular and cellular profiles between humans and dolphins, as well as their shared long lives, likely explain why humans and dolphins develop similar chronic aging-associated diseases. As dolphins age from 30 to 50 years old, they are more likely to develop chronic inflammation and dyslipidemia (Venn-Watson et al. 2011). Like humans, dolphins are susceptible to metabolic syndrome, including elevated insulin, glucose, cholesterol, triglycerides, and liver enzymes (Venn-Watson et al. 2015). The dolphin phenotype of metabolic syndrome also includes dysmetabolic iron overload syndrome, fatty liver disease, and nonalcoholic steatohepatitis, also called NASH (Mazzaro et al. 2012, Venn-Watson et al. 2012). Further, older dolphins can develop central neurodegenerative diseases, including development of amyloid-beta plaques and phosphorylated-tau tangles that parallel lesions present in people with Alzheimer's disease (Gunn-Moore et al. 2018). Based on their findings, Gunn-Moore et al. concluded that, "Dolphin, like man, an animal with exceptional longevity, might be one of very few natural models of Alzheimer's disease". All of these conditions have been documented in wild dolphins, supporting a wild-type susceptibility to chronic diseases. The many parallels between dolphins and humans support that discoveries made to in dolphins are relevant to human health.

For over 50 years, the United States Navy has cared for a population of approximately 100 dolphins. While the average lifespan of dolphins in the wild is 20 years, Navy dolphins on average live 32 years, more than fifty percent longer than wild dolphins. Approximately one-third of Navy dolphins are between 30 to 50 years old. Navy dolphins are more likely to have chronic conditions compared to wild dolphins living in Sarasota Bay, Fla.

In addition to differences in mean age, Navy and wild dolphins ingest different fish-based diets. Historically, Navy dolphins have been fed a diet of small, low-fat species, such as capelin and squid. Wild dolphins in Sarasota Bay ingest a large variety of fish, including larger, high-fat species, such as mullet and pinfish. It has been previously demonstrated that feeding Navy dolphins a modified diet resembling that of wild dolphins resulted in improved clinical indices of aging-associated conditions, including lowered ferritin and normalized glucose (Venn-Watson, Stephanie et al., 2015, "Increased Dietary Intake of Saturated Fatty Acid Heptadecanoic Acid (C17:0) Associated with Decreasing Ferritin and Alleviated Metabolic Syndrome In Dolphins", *PLOS ONE* 10(7): e0132117. doi:10.1371/journal.pone.0132117).

In addition to the above-cited normalized ferritin and glucose hypotheses, it was hypothesized that differences in fish diets may be drivers for the lower risk, in general, of chronic conditions in Sarasota Bay (wild) dolphins compared to Navy dolphins. It was further hypothesized that a modified fish diet could increase miR-29c and small molecules could be identified that upregulate miR-29c. As such, Navy dolphins were fed a modified, wild-type fish diet to assess changes in the serum metabolome and serum microRNA that may provide insight into potential targets and therapeutics for many chronic conditions, including neuromuscular disorders.

The above miR-29C hypothesis was tested in a study. This study examined the ability to identify small molecules in the dolphin serum that, when raised, independently predicted desired changed levels of microRNA targets for neuromuscular disorders. To do this, a modified, wild-type fish diet ("Modified Diet", see FIG. 1A) was fed to 20 Navy dolphins in netted enclosures within San Diego Bay. The Modified Diets of the 20 Navy dolphins were modified from a 75% capelin (plus 25% mix of squid, herring or mackerel) baseline diet, ("Baseline Diet", FIG. 1B), to a diet consisting of 25% capelin, 50% mullet, and 25% mix of squid, herring, or mackerel, FIG. 1A, while maintaining the same kilocalories. On blood collection days, modified diet dolphins were fed one-third of their daily diet in the morning after their routine overnight fast and 2 h postprandial, in-water, and trained blood samples were drawn (typically near 10:00 a.m.). An additional ten Navy dolphins were maintained on the Baseline Diet throughout the study period. There were no differences in age, sex, or body weight when comparing the two groups.

Two-hour post-prandial samples were collected from modified diet dolphins and baseline diet dolphins at baseline (month 0) and at three time points following the switch to the modified diet: months 1, 3, and 6. Blood samples from this study archived at −80° C. were submitted for global metabolomics and microRNA readouts.

A total of 120 archived serum samples from this study were analyzed for small molecules using global metabolomics. Briefly, serum extracts were prepared and analyzed using three methods: ultrahigh performance liquid chromatography-tandem mass spectroscopy (UPLC-MS/MS) with positive ion mode electrospray ionization (ESI), UPLC-MS/MS with negative ion mode ESI, and hydrophilic interaction liquid chromatography (UPLC-MS/MS).

The informatics system consisted of four major components, the Laboratory Information Management System (LIMS), the data extraction and peak-identification software, data processing tools for QC and compound identification, and a collection of information interpretation and visualization tools for use by data analysts. The hardware and software foundations for these informatics components were the LAN backbone, and a database server running Oracle 10.2.0.1 Enterprise Edition.

Raw data were extracted, peak-identified and QC processed using the above-listed hardware and software. Compounds were identified by comparison to library entries of purified standards or recurrent unknown entities. Biochemical identifications were based on three criteria: retention index within a narrow RI window of the proposed identification, accurate mass match to the library +/−10 ppm, and the MS/MS forward and reverse scores between the experimental data and authentic standards. Peaks were quantified using area-under-the-curve. A data normalization step was performed to correct variation resulting from instrument inter-day tuning differences.

Dolphin blood samples, preserved with PAXgene tubes stored at −80° C., from this study were analyzed for microRNA. MicroRNA (miRNA) are small, non-coding RNA molecules which function in RNA silencing and post-transcriptional regulation of gene expression. To assess potential gene expression changes driven by the modified fish diet, global microRNA (miRNA) species and quantities were measured in 120 blood samples collected from dolphins on the modified diet (cases) and controls at months 0, 1, 3, and 6. Analyses and interpretations included total miRNA species identified, conservation of dolphin miRNA with other species, differences in miRNA blood levels when comparing cases and controls (targeted miRNAs), and regulated genes and genetic pathways associated with miRNAs that changed during the modified diet. Briefly, samples were sequenced using Hiseq 2000 or 2500 Sequencing (Illumina Inc.), and data were filtered for unique families, quality, sequence patterns, length and known RNA classes. These clean data sequences were input into an miRbase Database containing reference sequences, and reads that were specific, known miRNAs were further mapped to the genome and expressed sequence tag. This resulted in identification of differentially expressed miRNAs between the modified diet and control groups, genome location clusters of pre-miRNAs, conservation of the identified miRNA with other species, and seed-sequence-based miRNA families.

Global metabolome and miRNA data were merged into a central database, and stepwise regression models were used, including all 466 known metabolites and 439 known miRNA to identify independent small molecule predictors of miR-29c. The strongest independent, linear small molecule predictors of miR-29c (defined as a P value<0.001 and $R^2>0.10$) were evaluated for direction of predicted values, and those in which increased small molecule values independently predicted increased miR-29c levels were selected.

Figure 1B:
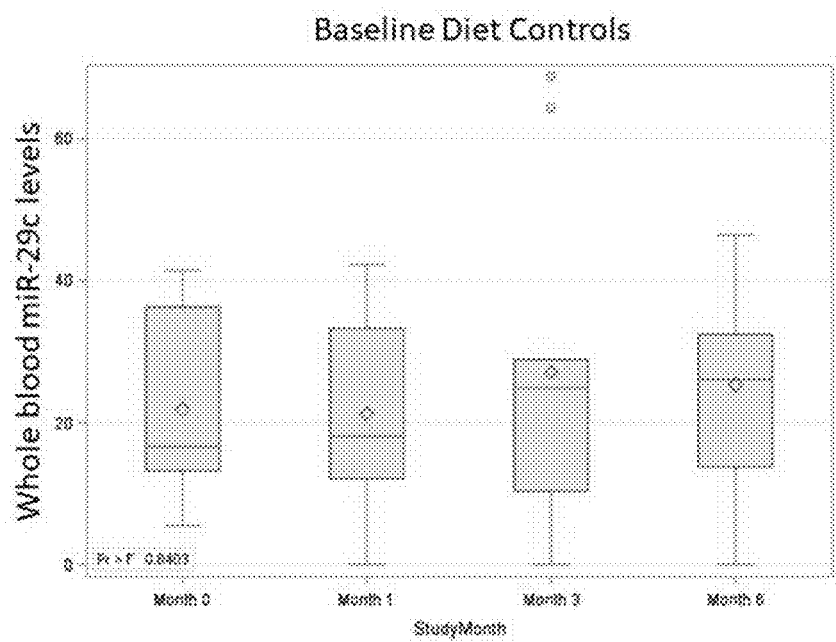
FIG. 1B can provides data on unchanged blood microRNA-29c levels in dolphins maintained on a baseline fish diet.

Using the above procedures, and referring to FIGS. 1A-1B, the results of the study can be seen. FIGS. 1A-1B are box and whisker plots of miR-29C whole blood levels for times Month 0, Month 1, Month 3 and Month 6, where the normalized miRNA expression values for each sample were calculated and expressed as relative fold changes to an internal standard. As known in the art, the ends of the box are the upper and lower quartiles, and the box vertically spans the range between the upper and lower quartiles. The two lines outside the box extend to the highest and lowest data observations. The observation mean is marked by a diamond inside the box, and the observation median is marked by a horizontal line inside the box, and there are a few data outliers (circles) outside the box and whiskers in FIGS. 1A-1B (as well as FIGS. 2A and 3A).

This study demonstrated a high rate of conservation of the identified miRNA in dolphin blood with cows and primates, including humans. Of 439 known miRNAs detected in dolphin blood, most miRNAs were conserved with cows (393, 89.5%); this was not surprising given the shared evolutionary phylogeny between dolphins and cows, which are both artiodactyls. Beyond cows and among all other species assessed, however, dolphin blood miRNAs were most highly conserved among primates, including humans (275, 62.6%), chimpanzee (233, 53.1%), orangutan (232, 52.8%), and rhesus monkey (230, 52.4%).

This study demonstrated a high rate of conservation of the identified high-priority metabolites in dolphin blood with humans. Approximately 100 of the 466 metabolites present in dolphin serum were found to be predictive of healthier metabolic states (data not shown). These molecules were cross-referenced with the Human Metabolome Database (www.hmdb.ca), and 83% of the 100 metabolites were characterized as either detected or assumed to be present in humans, including 2-hydroxymyristate and N-acetylhistamine.

By cross-referencing FIGS. 1A and 1B, it can be seen that miR-29c was successfully detected and quantified in dolphin blood. Further, miR-29c levels increased significantly among dolphins on the modified diet (Kruskal-Wallis P value>0.0003, FIG. 1A). This increase was not present among the control dolphins (Kruskal-Wallis P value>0.8403, FIG. 1B), which supports the hypothesis that the modified fish diet upregulated miR-29c.

Figure 2A:
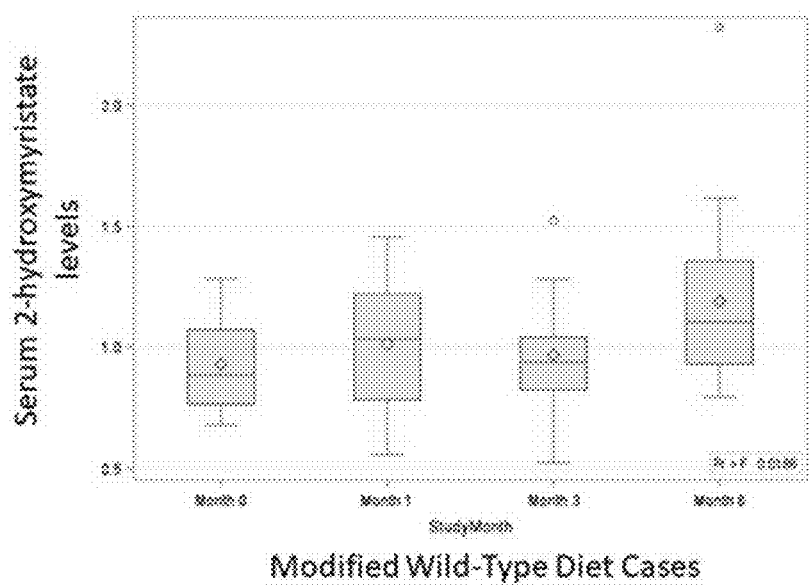
FIG. 2A can provide data on increasing serum 2-hydroxymyristate levels in dolphins on a modified fish diet.
Figure 2B:
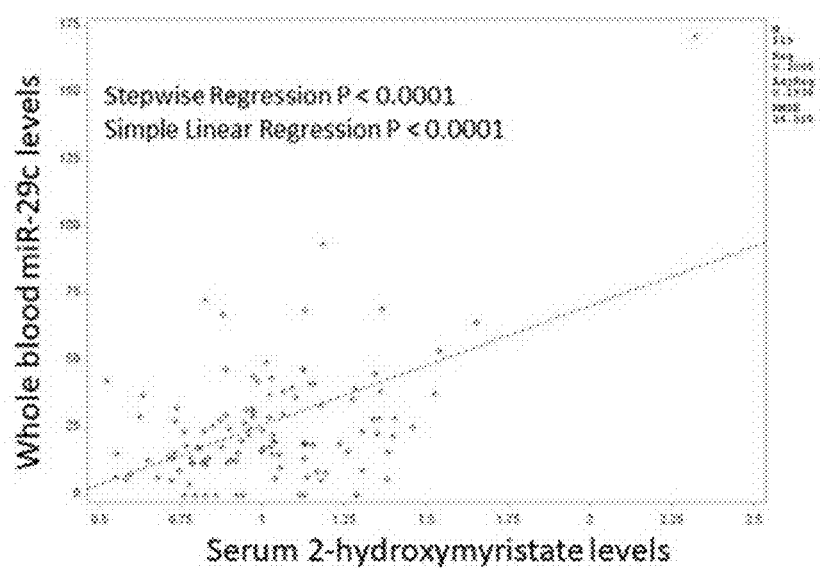
FIG. 2B can be a graph of whole blood miR-29c levels versus serum 2-hydroxymyristate levels, which can be used to illustrate that raised serum levels of 2-hydroxymyristate can independently predict a linear increase in miR-29c levels.
Figure 3A:
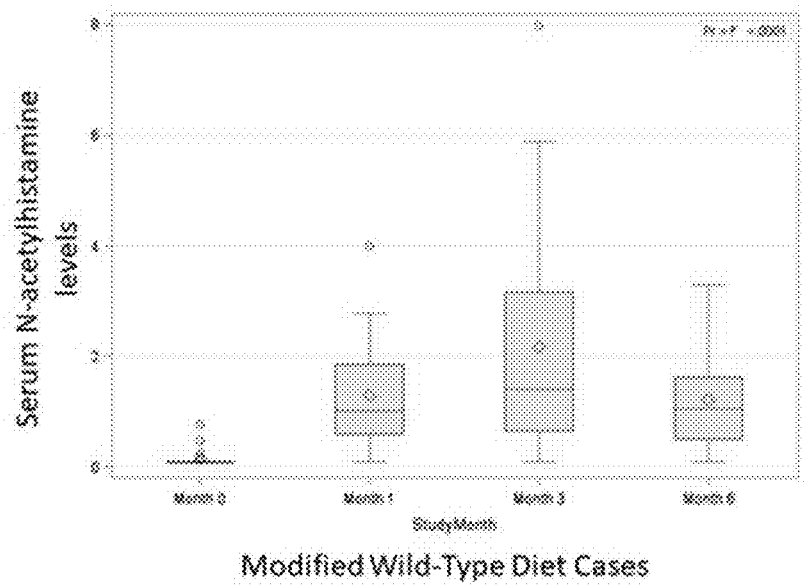
FIG. 3A can provide data on increasing serum N-acetylhistamine levels in dolphins on a modified fish diet.

With the results of the FIGS. 1A and 1B in mind, it was determined which biomolecules from the dolphin blood serum are functioning to upregulate the miR-29c. Of 466 known small molecule metabolites identified in dolphin serum, only two molecules were deemed as significant, independent and linear predictors of miR-29c. The first molecule is 2-hydroxymyristate. As shown in FIGS. 2A-2B, 2-hydroxymyristate, a monohydroxy fatty acid biomolecule, increased in the serum dolphins on the modified diet and this increase correlated with a linear increase in miR-29c (simple linear regression P<0.0001, $R^2=+0.20$). Further, using a stepwise regression model controlling for all other metabolites detected, increased serum 2-hydroxymyristate among dolphins on the modified diet independently predicted an increase in miR-29c (P<0.0001).

Figure 3B:
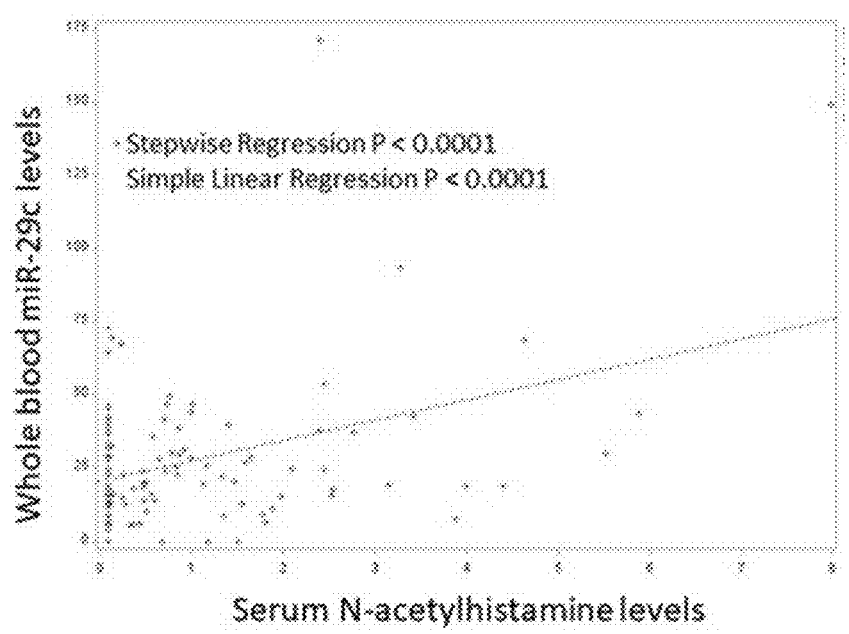
FIG. 3B can be a graph of whole blood miR-29c levels versus serum N-acetylhistamine, which can be used to illustrate that raised serum levels of N-acetylhistamine can independently predict a linear increase in miR-29c levels; and, FIG. 4 can be a bar graph, which can provide data on lowered alpha-smooth muscle actin levels by N-acetylhistamine in a primary human cell system mimicking myofibrosis. This activity was dose-dependent and was expected for an miR-29c upregulator.

The second of the two biomolecules that was deemed as a significant, independent and linear predictor of miR-29c was N-acetylhistamine. From looking at FIGS. 3A-3B, it can be seen that N-acetylhistamine, an amino acid and histadine metabolism intermediate, increased in the serum dolphins on the modified diet and this increase correlated with a linear increase in miR-29c (simple linear regression P<0.0001, $R^2=+0.13$). Further, using a stepwise regression model controlling for all other metabolites detected, increased serum N-acetylhistamine among dolphins on the modified diet independently predicted an increase in miR-29c (P<0.0001). The control Baseline Diet dolphin population did not demonstrate increases in either 2-hydroxymyristate or N-acetylhistamine (not shown).

This study successfully demonstrated that a modified diet could effectively raise blood miR-29c approximately 2-fold, and increased serum levels of two small molecules (increased 2-hydroxymyristate by 50% and N-acetylhistamine by 5-fold) each independently predicted upregulation of miR-29c.

Example 2

It was also hypothesized that targeted small molecule metabolites identified in Example 1 (2-hydroxymyristate and N-acetylhistamine) would be present at higher levels in healthy wild dolphins living in Sarasota Bay, Fla., compared to Navy dolphins, and that wild dolphin serum levels may be used to define optimal levels of 2-hydroxymyristate and N-acetylhistamine in dolphins.

To test this additional hypothesis, routine, fasted serum samples collected throughout 26 Navy dolphins' lifespans and archived at −80° C. were submitted for global metabolomics. The sample set targeted one sample for each dolphin's year of life, resulting in 355 samples for the study with paired clinical pathology data. In addition, single serum samples from 38 healthy wild dolphins living in Sarasota Bay, Fla. were included in the sample set. Methodology for metabolomics analyses were the same as described under Example 1 described above.

Welch's two-sample t-tests were performed to compare metabolite quantities between Navy dolphins and wild dolphins, and a P value≤0.05 was used to define significance.

Sarasota Bay wild dolphins had 1.23 times higher serum levels of 2-hydroxymyristate (P=0.004) and 8.93 times higher levels of N-acetylhistamine (P=0.0001) compared to Navy dolphins.

This study successfully demonstrated that targeted therapeutic serum levels of individuals with low miR-29c levels could be a 1.2-fold increase in 2-hydroxymyristate and a 9-fold increase in N-acetylhistamine.

Example 3

Example 1 identified two serum biochemicals that can serve as biomarkers and candidate therapeutics for neuromuscular conditions, in part by raising miR-29c levels. As previously discussed, upregulation of miR-29c can decrease fibrosis in the muscle of models for Duchenne muscular dystrophy (Zanotti et al., cited above). Because higher serum levels of N-acetylhistamine were independently predictive of raised miR-29c levels, it was hypothesized that N-acetylhistamine would effectively lower fibrosis in human cell lines mimicking various fibrotic diseases.

Phenotypic profiling, including antifibrotic activity, was conducted across 12 human primary cell-based systems as part of DiscoverX's BioMAP Diversity Plus program. These systems are designed to model complex human tissue and disease biology of the vasculature, skin, lung, and inflammatory tissues. Quantitative measurements of biomarker activities across this broad panel were used to assess each biochemical's antifibrotic activity at four concentrations (740 nm and 2.2, 6.7 and 20 μM). Cell-based activated systems were incubated with pure N-acetylhistamine for 24 to 72 hours. Protein-based biomarkers from activated cell systems were measured and compared with controls. Biomarker activities were annotated when 2 or more consecutive concentrations change in the same directions relative to vehicle controls, were outside of the significance envelope and had at least one concentration with an effect size >20% (log 10 ratio)>0.1.

Figure 4:
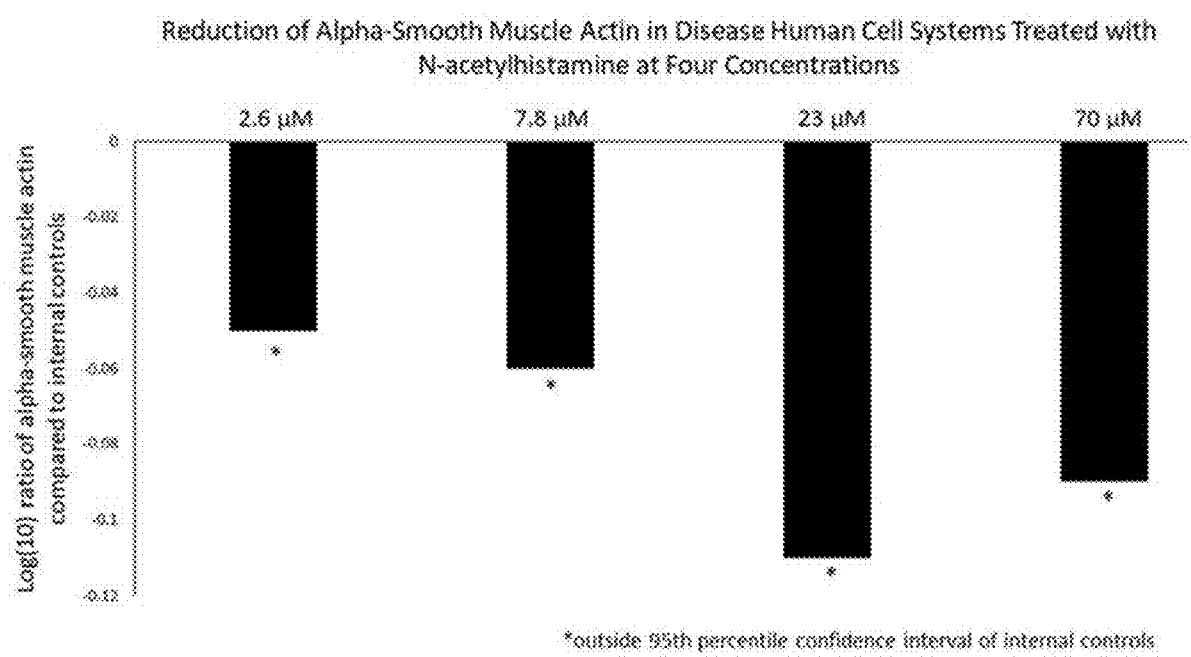

In our study, N-acetylhistamine, an amino acid involved in histadine metabolism, caused a significant and dose-dependent decrease in alpha-smooth muscle actin (α-SMA), a protein involved in muscle contraction, cell motility, structure and integrity and a marker for activated myofibroblast phenotype, in a human cell system mimicking myofibroblast development. In this system, human primary lung fibroblasts were stimulated with TGF-β and TNF-α and incubated with the test agent, drug control, or vehicle control for 24 hours. A negative, non-stimulated system was also included. N-acetylhistamine, at 2.6, 7.8, 23, and 70 μM concentrations significantly decreased α-SMA compared to internal controls (FIG. 4). Antifibrotic activity demonstrated by N-acetylhistamine, in this human cell system is consistent with this biochemical's predicted upregulation of miR-29c from Example 1 and anticipated antifibrotic activity.

This proof of concept study successfully demonstrated a serum-based small molecule (N-acetylhistamine), identified in dolphin serum, as a means to detect, prevent and treat an expected component of a neuromuscular disorder (myofibrosis) regulated by miR-29c, at relevant therapeutic concentrations ranging from 2.6 to 70 μM.

In summary, results from our examples demonstrate that 1) targeted biochemicals were successfully identified in serum in which raised levels independently predicted raised miR-29c levels (a desired outcome for a therapeutic), 2) wild dolphins had higher levels of these targeted biochemicals compared to Navy animals, and 3) we could successfully demonstrate relevant therapeutic activities in human cell-based systems mimicking myofibrosis, an expected outcome for an miR-29c upregulator.

Monohydroxy fatty acids or histadine metabolism intermediates described herein can be present in serum or plasma due to either ingestion of food products or endogenous production. Thousands of small molecule biochemicals can be detected and measured in serum of animals, including dolphins and humans. Metabolomics, the study of biochemicals and their biologically relevant roles, is a relatively novel field of study. Due to the large number of biochemicals present and high potential variation of biochemicals driven by complex diets, environments, genetics, and long-term medications in human populations, identifying biochemicals with the greatest biomarker and therapeutic potential has been complicated. Based upon the results using the methods of the embodiments, it can be proposed that monohydroxy fatty acids or histadine metabolism intermediates described herein may be key players in detecting, preventing, and treating neuromuscular disorders, including muscular dystrophies, peripheral motor neuron diseases, motor neuron diseases, neuromuscular junction diseases, myopathies, metabolic diseases of the muscle, amyotrophic lateral sclerosis, Parkinson's disease, motor neuron diseases, Huntington's disease, spinocerebellar ataxia, and spinal muscular atrophy, as well as other conditions caused or exacerbated by low miR-29c.

To take advantage of these benefits, monohydroxy fatty acids or histadine metabolism intermediates can be used in a supplement, medical food, food additive, food fortifier, beverage additive, beverage fortifier, or pharmaceutical in any form, including as a tablet, encapsulated pill, gel cap pill, liquid suspension, spray, and powder. Additionally, diagnostic tests and assays for small molecule biochemicals described herein in human and animal samples (including blood (serum, plasma, and erythrocyte membranes), urine, and feces) can be used to detect low monohydroxy fatty acids or histadine metabolism intermediates and to continually monitor small molecule metabolite levels in patients. The use of monohydroxy fatty acids or histadine metabolism intermediates can prevent, stem, and treat: neuromuscular disorders, including muscular dystrophies, peripheral motor neuron diseases, motor neuron diseases, neuromuscular junction diseases, myopathies, metabolic diseases of the muscle, amyotrophic lateral sclerosis, multiple sclerosis, Parkinson's disease, motor neuron diseases, Huntington's disease, spinocerebellar ataxia, and spinal muscular atrophy, as well as other conditions caused or exacerbated by low miR-29c.

The data support the benefit of and feasibility for raised levels of monohydroxy fatty acids or histadine metabolism intermediates to raise key protective and therapeutic factors for neuromuscular conditions, including raised miR-29c and reduced myofibroblast development.

The data demonstrate beneficial activity of targeted therapeutics at specific and relevant concentrations ranging 2.6 μM to at 70 μM, with targeted increases ranging from 1.2 to 9 times greater levels and most beneficial effects anticipated by at least 2-fold increases in serum levels. Dosing of monohydroxy fatty acids or histadine metabolism intermediates to achieve these serum, plasma, cell, or tissue levels is expected to confer the observed beneficial effects.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances, where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method of treatment of neuromuscular disorders, at least one of the neuromuscular disorders being selected from a group consisting of muscular dystrophies, peripheral motor neuron diseases, motor neuron diseases, neuromuscular junction diseases, myopathies, metabolic diseases of the muscle, amyotrophic lateral sclerosis, multiple sclerosis, Parkinson's disease, motor neuron diseases, Huntington's disease, spinocerebellar ataxia, or spinal muscular atrophy, or conditions that cause or exacerbate neuromuscular disorders, the conditions comprising low miR-29c, the method comprising:

administering to a patient in need thereof, an effective amount of one or more monohydroxy fatty acids or histadine metabolism intermediates, or pharmaceutically acceptable salts, solvates, stereoisomers, or esters thereof.

2. The method of claim 1, wherein the one or more monohydroxy fatty acids or histadine metabolism intermediates is 2-hydroxymyristate or N-acetylhistamine, and combinations thereof.

3. The method of claim 2, wherein the one or more monohydroxy fatty acids or histadine metabolism intermediates has a low molecular weight of <900 Daltons, and meets Lipinski's rule of five.

4. The method of claim 3, wherein the one or more monohydroxy fatty acids or histadine metabolism intermediates or pharmaceutically acceptable salts, solvates, stereoisomers, or esters thereof is provided as a pharmaceutical composition in a unit dosage form comprising the one or more small molecule biochemicals or pharmaceutically acceptable salts thereof and a pharmaceutically acceptable carrier.

5. The method of claim 3, wherein the unit dosage form comprises from 0.01 mg to 10000 mg of the one or more monohydroxy fatty acids or histadine metabolism intermediates or pharmaceutically acceptable salts thereof.

6. The method of claim 3, wherein the one or more small molecule biochemicals is 2-hydroxymyristate or N-acetylhistamine.

7. The method of claim 6, wherein the pharmaceutical composition comprises a plurality of different monohydroxy fatty acids or histadine metabolism intermediates.

8. The method of claim 7, wherein from 2.5 mg to 50 mg of the one or more monohydroxy fatty acids or histadine metabolism intermediates or pharmaceutically acceptable salts, solvates, stereoisomers, or esters thereof is administered to the patient, per 1 kg of body weight, per day.

9. The method of claim 8, wherein the one or more monohydroxy fatty acids or histadine metabolism intermediates or pharmaceutically acceptable salts, solvates, stereoisomers, or esters thereof is administered to the patient once per day.

* * * * *